(12) United States Patent
Ashley et al.

(10) Patent No.: US 6,894,036 B2
(45) Date of Patent: May 17, 2005

(54) 4-DEDIMETHYLAMINOTETRACYCLINE DERIVATIVES

(75) Inventors: Robert Ashley, Newtown, PA (US); Joseph J. Hlavka, Suffern, NY (US)

(73) Assignee: CollaGenex Pharmaceuticals, Incorporated, Newton, PA (US)

( * ) Notice: Subject to any disclaimer, the term of this patent is extended or adjusted under 35 U.S.C. 154(b) by 0 days.

(21) Appl. No.: 10/458,076

(22) Filed: Jun. 10, 2003

(65) Prior Publication Data

US 2004/0002481 A1 Jan. 1, 2004

(Under 37 CFR 1.47)

Related U.S. Application Data

(60) Division of application No. 09/911,861, filed on Jul. 24, 2001, now Pat. No. 6,638,922, which is a continuation-in-part of application No. 09/573,654, filed on May 18, 2000, now Pat. No. 6,506,740, which is a continuation-in-part of application No. 09/479,604, filed on Jan. 7, 2000, now abandoned, which is a continuation-in-part of application No. 09/195,013, filed on Nov. 18, 1998, now abandoned.

(51) Int. Cl.$^7$ .................. A61K 31/65; C07C 237/26
(52) U.S. Cl. ........................ 514/152; 552/203
(58) Field of Search .................... 552/203; 514/152

(56) References Cited

U.S. PATENT DOCUMENTS

| | | |
|---|---|---|
| 2,786,077 A | 3/1957 | Stephens, Jr. |
| 2,970,087 A | 1/1961 | Beck et al. |
| 2,976,318 A | 3/1961 | Blackwood |
| 3,026,248 A | 3/1962 | Noseworthy et al. |
| 3,029,284 A | 4/1962 | Gordon |
| 3,036,120 A | 5/1962 | Hammer et al. |
| 3,042,716 A | 7/1962 | Blackwood et al. |
| 3,043,875 A | 7/1962 | Beereboom et al. |
| 3,047,626 A | 7/1962 | Stephens, Jr. et al. |
| 3,069,467 A | 12/1962 | Beereboom et al. |
| 3,109,007 A | 10/1963 | Blackwood et al. |
| 3,146,265 A | 8/1964 | Scott et al. |
| 3,159,675 A | 12/1964 | Esse et al. |
| 3,180,889 A | 4/1965 | Hlavka et al. |
| 3,239,499 A | 3/1966 | Rennhard et al. |
| 3,265,732 A | 8/1966 | Miller et al. |
| 3,304,227 A | 2/1967 | Loveless |
| 3,345,370 A | 10/1967 | Esse et al. |
| 3,359,160 A | 12/1967 | Gordon |
| 3,360,559 A | 12/1967 | McCormick et al. |
| 3,375,276 A | 3/1968 | Neidleman et al. |
| 3,428,679 A | 2/1969 | Rondelet |
| 3,455,800 A * | 7/1969 | Bitha et al. ............. 204/157.82 |
| 3,502,660 A | 3/1970 | Bulter et al. |
| 3,502,696 A | 3/1970 | Conover |
| 3,509,184 A | 4/1970 | Conover et al. |
| 3,515,731 A | 6/1970 | Conover |
| 3,609,188 A | 9/1971 | Esse |
| 3,622,627 A | 11/1971 | Blackwood et al. |
| 3,697,552 A | 10/1972 | Conover et al. |
| 3,772,363 A | 11/1973 | Conover et al. |
| 3,824,285 A | 7/1974 | Blackwood et al. |
| 3,829,453 A | 8/1974 | Conover et al. |
| 3,849,493 A | 11/1974 | Canover et al. |
| 4,419,365 A | 12/1983 | McLachlan |
| 4,704,383 A | 11/1987 | McNamara et al. |
| 4,925,833 A | 5/1990 | McNamara et al. |
| 5,122,519 A | 6/1992 | Ritter |
| 5,223,248 A | 6/1993 | McNamara et al. |
| 5,308,839 A | 5/1994 | Golub et al. |
| 5,321,017 A | 6/1994 | Golub et al. |
| 5,371,076 A | 12/1994 | Lee et al. |
| 5,459,135 A | 10/1995 | Golub et al. |
| 5,523,297 A | 6/1996 | Pruzanski et al. |
| 5,529,990 A | 6/1996 | Hlavka et al. |
| 5,532,227 A | 7/1996 | Golub et al. |
| 5,563,130 A | 10/1996 | Backer et al. |
| 5,567,693 A | 10/1996 | Backer et al. |
| 5,574,026 A | 11/1996 | Backer et al. |
| 5,773,430 A | 6/1998 | Simon et al. |
| 5,789,395 A | 8/1998 | Amin et al. |
| 5,849,290 A | 12/1998 | Brown et al. |
| 5,919,775 A | 7/1999 | Amin et al. |
| 5,998,390 A | 12/1999 | Ramamurthy et al. |
| 6,043,231 A * | 3/2000 | Pruzanski et al. ......... 514/152 |
| 6,277,061 B1 * | 8/2001 | Golub et al. ............. 514/152 |
| 6,319,910 B1 * | 11/2001 | Amin et al. ............. 514/152 |
| 6,455,583 B1 * | 9/2002 | Pflugfelder et al. ........ 514/528 |
| RE38,386 E * | 1/2004 | Berman .................. 514/152 |

FOREIGN PATENT DOCUMENTS

| | | |
|---|---|---|
| EP | 0 464 932 A | 1/1992 |
| WO | 94-19493 | 9/1994 |
| WO | 99/30720 | 6/1999 |
| WO | 00/28983 | 5/2000 |

OTHER PUBLICATIONS

Mitscher, "Chemical Transformations of the Tetracycline Family," The Chemistry of Tetracyclines, Chapter 6:165–218, 1996.

Rogalski, W. "Chemical Modification of the Tetracyclines," Chapter 5:179–315, 1996.

Katiyar, SK, Edlind, TD, "Enhanced Antiparasitic Activity of Lipophilic Tetracyclines: Role of Uptake," Antimicrobial Agents and Chemotherapy, 35(11):2198–2202 (1991).

(Continued)

Primary Examiner—Barbara P. Badio
(74) Attorney, Agent, or Firm—Hoffmann & Baron, LLP

(57) ABSTRACT

The present invention provides new chemically modified 4-dedimethylaminotetracycline compounds that can be substituted with aryl, alkenyl, or alkynyl groups. The 7, 8, and/or 9 positions and methods for preparing such compounds. Other tetracycline compounds include the 4-dedimethylaminotetracycline derivatives with an oxime group, NH-Alkyl, or N—NH-Alkyl group substituted at the C4 position as well as C2 Mannich derivatives. The present invention also provides a method of treating a mammal suffering from conditions or diseases by administering to the mammal an effective amount of the new chemically modified tetracycline compounds.

4 Claims, 1 Drawing Sheet

OTHER PUBLICATIONS

Forloni et al. "Anti–amyloidogenic activity of tetracyclines: studies in vitro," FEBS Letters 487:404–407 (2001).

Tikka et al. "Minocycline Provides Neuroprotection Against N–Methyl–D—aspartate Neurotoxicity by Inhibiting Microglia," The Journal of Immunology, 166:7527–7533 (2001).

Tikka et al. "Minocycline, a Tetracycline Derivative, is Neuroprotective against Excitotoxicity by Inhibiting Activatin and Proliferation of Microglia," The Journal of Neuroscience 21(8):2580–2588 (2001).

Chen et al. "Minocycline inhibits caspase–1 and caspase–3 expression and delays mortality in a transgenic mouse model of Huntington disease," Nature Medicine, 6 (7): 797–801 (2000).

Yrjanheikki et al."A Tetracycline derivative, minocycline, reduces inflammation and protects against focal cerebral ischemia with a wide therapeutic window," Proc. Natl. Acad. Sci. 96 (23):13496–500 (1999).

Howlett et al. "Common structural features determine the effectiveness of carvedilol, daunomycin and rolitetracycline as inhibitors of Alzheimer β–amyloid fibril formation," Biochem. J. 343:419–423 (1999).

Tagliavini et al. "Tetracycline Affects Abnormal Properties of Synthetic PrPPeptides and PrPSc in vitro," Journal of Molecular Biology 300 (5):1309–22 (2000).

Yrjanheikki et al. "Tetracyclines inhibit microglial activation and are neuroprotective in global brain ischemia," Proc. Natl. Acad. Sci. 95(26):15769–74 (1998).

Dubois et al. "Toxicity in a double–blind, placebo–controlled pilot trial with D–penicillamine and metacycline in secondary progressive multiple sclerosis," Multiple Sclerosis, 4:74–78 (1998).

Paemen et al. "The Gelatinase Inhibitory Activity of Tetracycline and Chemically Modified Tetracycline Analogues as Measured by a Novel Microtiter Assay for Inhibitors," Biochemical Pharmacology, 52:105–111, (1996).

Goodwin et al. "Management of Lyme Disease," Clinical Pharmacy 9:192–205 (1990).

Snavely et al. "The neurotoxicity of antibacterial agents," Ann. Intern. Med.101(1):92–104 (1984).

Koza "Synthesis of 7–Substituted Tetracycline Derivatives," Organic Letters; 2(6):815–817 (2000).

* cited by examiner

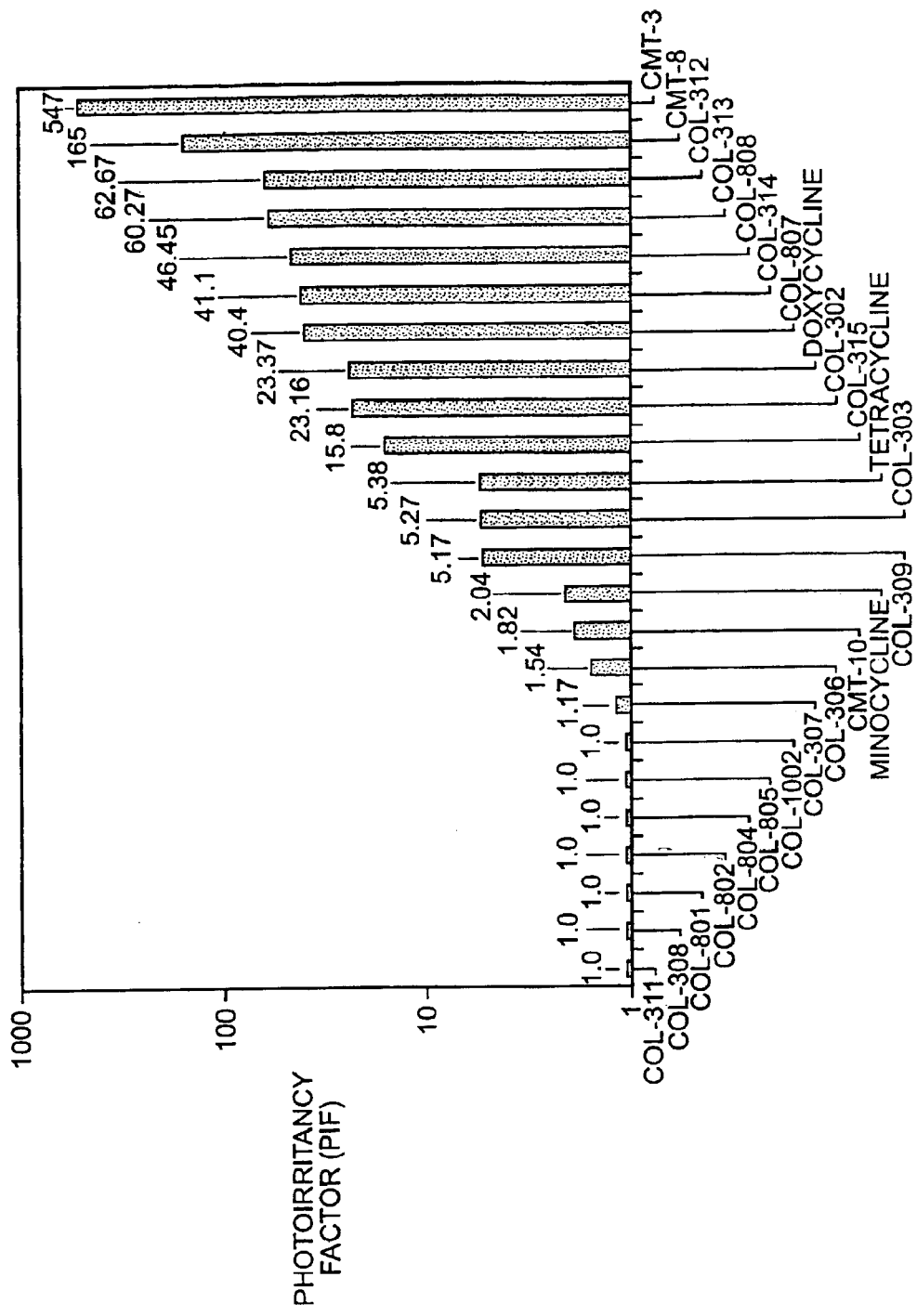
FIG. 1 PHOTOTOXICITY INDEX

4-DEDIMETHYLAMINOTETRACYCLINE DERIVATIVES

The present application is a divisional of Ser. No. 09/911,861, filed on Jul. 24, 2001, now U.S. Pat. No. 6,638,922 which is a continuation-in-part of Ser. No. 09/573,654, filed May 18, 2000 now U.S. Pat. No. 6,506,740 which is a continuation-in-part of Ser. No. 09/479,604, filed Jan. 7, 2000, now abandoned which is a continuation-in-part of Ser. No. 09/195,013 filed Nov. 18, 1998, now abandoned all of which are incorporated herein by reference.

FIELD OF INVENTION

The present invention relates to novel 4-dedimethylaminotetracycline derivatives, methods for producing the novel derivatives and methods of using these derivatives.

BACKGROUND OF THE INVENTION

The compound, tetracycline, exhibits the following general structure:

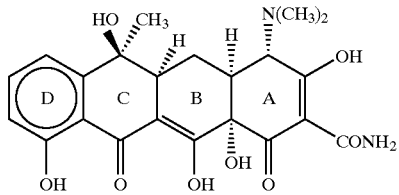

Structure A

The numbering system of the ring nucleus is as follows:

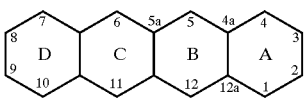

Structure B

Tetracycline as well as the 5-OH (Terramycin) and 7-Cl (Aureomycin) derivatives exist in nature, and are well known antibiotics. Natural tetracyclines may be modified without losing their antibiotic properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5–9 of the tetracycline ring system may be modified without the complete loss of antibiotic properties. Changes to the basic ring system or replacement of the substituents at positions 1–4 and 10–12, however, generally lead to synthetic tetracyclines with substantially less or effectively no antimicrobial activity. Some examples of chemically modified non-antimicrobial tetracyclines (hereinafter CMT) include 4-dedimethylaminotetracyline, 4-dedimethylaminosancycline (6-demethyl-6-deoxy-4-dedimethylaminotetracycline), 4-dedimethylaminominocycline (7-dimethylamino-4-dedimethylaminotetracycline), and 4-dedimethylaminodoxycycline (5-hydroxy-6-deoxy-4-dedimethyaminotetracycline).

Some 4-dedimethylaminotetracyline derivatives are disclosed in U.S. Pat. Nos. 3,029,284 and 5,122,519. They include 6-demethyl-6-deoxy-4-dedimethylaminotetracycline and 5-hydroxy-6-deoxy-4-dedimethylaminotetracycline with hydrogen and other substituents at the C7, and the C9 positions on the D ring. These substituents include amino, nitro, di (lower alkyl) amino, and mono (lower alkyl) amino or halogen. The 6-demethyl-6-deoxy-4-dedimethylaminotetracycline derivatives and 5-hydroxy-6-deoxy-4-dedimethylaminotetracycline derivatives are said to be useful as antimicrobial agents.

Other 4-dedimethylaminotetracycline derivatives with an oxime group at the C4 position on the A ring are disclosed in U.S. Pat. Nos. 3,622,627 and 3,824,285. These oxime derivatives have hydrogen and halogen as substituents at the C7 position and include 7-halo-6-demethyl-6-deoxy-4-dedimethylamino-4-oximinotetracycline, and 7-halo-5-hydroxy-6-deoxy-4-dedimethylamino-4-oximinotetracycline.

Alkylamino (NH-alkyl), and alkylhydrazone (N—NH-alkyl) groups have been substituted on the A ring at the C4 position of 4-dedimethylaminotetracycline. These compounds are known for their antimicrobial properties. See U.S. Pat. Nos. 3,345,370, 3,609,188, 3,622,627, 3,824,285, 3,622,627, 3,502,660, 3,509,184, 3,502,696, 3,515,731, 3,265,732, 5,122,519, 3,849,493, 3,772,363, and 3,829,453.

In addition to their antimicrobial properties, tetracyclines have been described as having a number of other uses. For example, tetracyclines are also known to inhibit the activity of collagen destructive enzymes, such as matrix metalloproteinases (MMP), including collagenase (MMP-1), gelatinase (MMP-2) and stromelysin (MMP-3). Golub et al., *J. Periodont. Res.* 20:12–23 (1985); Golub et al. *Crit. Revs. Oral Biol. Med.* 2: 297–322 (1991); U.S. Pat. Nos. 4,666,897; 4,704,383; 4,935,411; 4,935,412. Also, tetracyclines have been known to inhibit wasting and protein degradation in mammalian skeletal muscle, U.S. Pat. No. 5,045,538, and to enhance IL-10 production in mammalian cells.

Furthermore, tetracyclines were reported to enhance bone protein synthesis in U.S. Pat. No. Re. 34,656, and to reduce bone resorption in organ culture in U.S. Pat. No. 4,704,383.

Similarly, U.S. Pat. No. 5,532,227 to Golub et al, discloses that tetracyclines can ameliorate the excessive glycosylation of proteins. In particular, tetracyclines inhibit the excessive collagen cross linking which results from excessive glycosylation of collagen in diabetes.

Tetracyclines are known to inhibit excessive phospholipase $A_2$ activity involved in inflammatory conditions such as psoriasis as disclosed in U.S. Pat. No. 5,532,227. In addition, tetracyclines are also known to inhibit cycloxygenase-2 (COX-2), tumor necrosis factor (TNF), nitric oxide and IL-1 (interleukin-1).

These properties cause the tetracyclines to be useful in treating a number of diseases. For example, there have been a number of suggestions that tetracyclines, including non-antimicrobial tetracyclines, are effective in treating arthritis. See, for example, Greenwald, et al. "Tetracyclines Suppress Metalloproteinase Activity in Adjuvant Arthritis and, in Combination with Flurbiprofen, Ameliorate Bone Damage," *Journal of Rheumatology* 19:927–938(1992); Greenwald et al., "Treatment of Destructive Arthritic Disorders with MMP Inhibitors: Potential Role of Tetracyclines in Inhibition of Matrix Metalloproteinases: *Therapeutic Potential,*" *Annals of the New York Academy of Sciences* 732: 181–198 (1994); Kloppenburg, et al. "Minocycline in Active Rheumatoid Arthritis," *Arthritis Rheum* 37:629–636(1994); Ryan et al., "Potential of Tetracycline to Modify Cartilage Breakdown in Osteoarthritis," *Current Opinion in Rheumatology* 8: 238–247(1996); O'Dell et al, "Treatment of Early Rheumatoid Arthritis with Minocycline or Placebo," *Arthritis. Rheum.* 40:842–848(1997).

Tetracyclines have also been suggested for use in treating skin diseases. For example, White et al., *Lancet*, April 29, p. 966 (1989) report that the tetracycline minocycline is effective in treating dystrophic epidermolysis bullosa, which is a life-threatening skin condition believed to be related to excess collagenase.

Furthermore, studies have also suggested that tetracyclines and inhibitors of metalloproteinases inhibit tumor progression, DeClerck et al., *Annals N.Y. Acad. Sci.*, 732: 222–232 (1994), bone resorption, Rifkin et al., *Annals N.Y. Acad. Sci.*, 732: 165–180 (1994), angiogenesis, Maragoudakis et al., *Br. J. Pharmacol.*, 111: 894–902 (1994), and may have anti-inflammatory properties, Ramamurthy et al., *Annals N.Y. Acad. Sci.*, 732, 427–430 (1994).

Based on the foregoing, tetracyclines have been found to be effective in treating numerous diseases and conditions. Therefore, there is a need for new and even more useful 4-dedimethylaminotetracycline derivatives.

SUMMARY OF THE INVENTION

It has now been discovered that these and other objectives can be achieved by tetracycline compounds of the formulae:

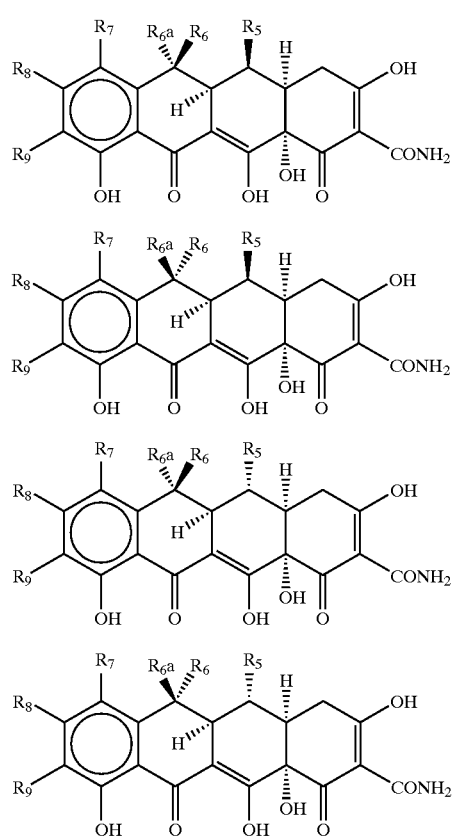

Structure C

Structure D

Structure E

Structure F wherein $R_7$ is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; $R_{6\text{-a}}$ is selected from the group consisting of hydrogen and methyl; $R_6$ and $R_5$ are selected from the group consisting of hydrogen and hydroxyl; $R_8$ is selected from the group consisting of hydrogen and halogen; $R_9$ is selected from the group consisting of hydrogen, amino, azido, nitro, acylamino, hydroxy, ethoxythiocarbonylthio, mono(lower alkyl)amino, halogen, diazonium, di(lower alkyl)amino and $RCH(NH_2)CO$; R is hydrogen or lower alkyl; and pharmaceutically acceptable and unacceptable salts thereof; with the following provisos: when either $R_7$ and $R_9$ are hydrogen then $R_8$ must be halogen; and when $R_{6\text{-a}}$, $R_6$, $R_5$ and $R_9$ are all hydrogen and $R_7$ is hydrogen, amino, nitro, halogen, dimethylamino or diethylamino, then $R_8$ must be halogen; and when $R_{6\text{-a}}$ is methyl, $R_6$ and $R_9$ are both hydrogen, $R_5$ is hydroxyl and $R_7$ is hydrogen, amino, nitro, halogen or diethylamino, then $R_8$ is halogen; and when $R_{6\text{-a}}$ is methyl, $R_6$ is hydroxyl, $R_5$, $R_7$ and $R_9$ are all hydrogen, then $R_8$ must be halogen; and when $R_{6\text{-a}}$, $R_6$ and $R_5$ are all hydrogen, $R_9$ is methylamino and $R_7$ is dimethylamino, then $R_8$ must be halogen; and when $R_{6\text{-a}}$ is methyl, $R_6$ is hydrogen, $R_5$ is hydroxyl, $R_9$ is methylamino and $R_7$ is dimethylamino, then $R_8$ must be halogen; and when $R_{6\text{-a}}$ is methyl, $R_6$, $R_5$ and $R_9$ are all hydrogen and $R_7$ is cyano, then $R_8$ must be halogen.

In another embodiment, the invention provides a tetracycline compound of the formulae:

Structure G

Structure H

Structure I

Structure J wherein $R_7$ is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; $R_{6\text{-a}}$ is selected from the group consisting of hydrogen and methyl; $R_6$ and $R_5$ are selected from the group consisting of hydrogen and hydroxyl; $R_4$ is selected from the group consisting of NOH, N—NH-A, and NH-A, where A is a lower alkyl group; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, di(lower alkyl)amino and RCH(NH$_2$)CO; R is hydrogen or lower alkyl; and pharmaceutically acceptable and unacceptable salts thereof; with the following provisos: when R4 is NOH, N—NH-alkyl or NH-alkyl and R7, R6-a, R6, R5, and R9 are all hydrogen, then R8 must be halogen; and when R4 is NOH, R6-a is methyl, R6 is hydrogen or hydroxyl, R7 is halogen, R5 and R9 are both hydrogen, then R8 must be halogen; and when R4 is N—NH-alkyl, R6-a is methyl, R6 is hydroxyl and R7, R5, R9 are all hydrogen, then R8 must be halogen; and when R4 is NH-alkyl, R6-a, R6, R5 and R9 are all hydrogen, R7 is hydrogen, amino, mono(lower alkyl) amino, halogen, di(lower alkyl)amino or hydroxyl, then R8 must be halogen; and when R4 is NH-alkyl, R6-a is methyl, R6 and R9 are both hydrogen, R5 is hydroxyl, and R7 is mono(lower alkyl)amino or di(lower alkyl)amino, then R8 must be halogen; and when R4 is NH-alkyl, R6-a is methyl, R6 is hydroxy or hydrogen and R7, R5, and R9 are all be hydrogen, then R8 must be halogen.

In yet another embodiment, the invention provides a 4-dedimethylamino tetracycline compound having general formulae (I) through (IV):

General Formula (I)

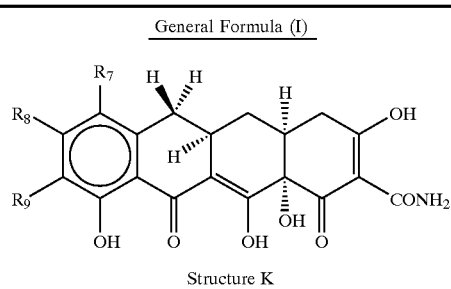

Structure K wherein R7, R8, and R9 taken together in each case, have the following meanings:

| R7 | R8 | R9 |
|---|---|---|
| azido | hydrogen | hydrogen |
| dimethylamino | hydrogen | azido |
| hydrogen | hydrogen | amino |
| hydrogen | hydrogen | azido |
| hydrogen | hydrogen | nitro |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| hydrogen | hydrogen | ethoxythiocarbonylthio |
| dimethylamino | hydrogen | acylamino |
| dimethylamino | hydrogen | diazonium |
| dimethylamino | chloro | amino |
| hydrogen | chloro | amino |
| amino | chloro | amino |
| acylamino | chloro | acylamino |
| amino | chloro | hydrogen |
| acylamino | chloro | hydrogen |
| monoalkylamino | chloro | amino |
| nitro | chloro | amino |
| dimethylamino | chloro | acylamino |
| dimethylamino | chloro | dimethylamino |
| dimethylamino | hydrogen | hydrogen |
| hydrogen | hydrogen | dimethylamino | and

General Formula (II)

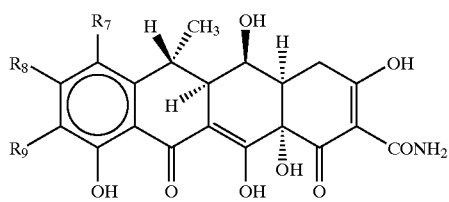

Structure L

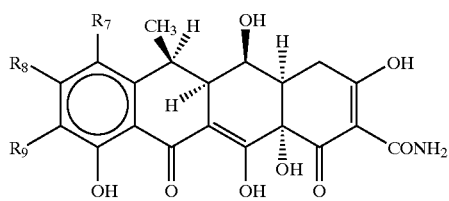

Structure M

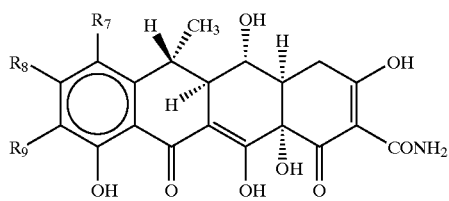

Structure N

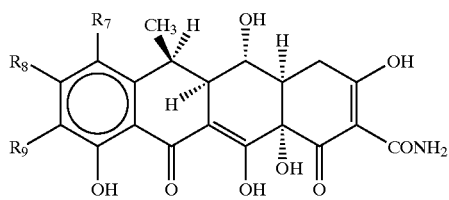

Structure O wherein R7, R8, and R9 taken together in each case, have the following meanings:

| R7 | R8 | R9 |
|---|---|---|
| azido | hydrogen | hydrogen |
| dimethylamino | hydrogen | azido |
| hydrogen | hydrogen | amino |
| hydrogen | hydrogen | azido |
| hydrogen | hydrogen | nitro |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| hydrogen | hydrogen | ethoxythiocarbonylthio |
| dimethylamino | hydrogen | acylamino |
| hydrogen | hydrogen | diazonium |
| hydrogen | hydrogen | dimethylamino |
| diazonium | hydrogen | hydrogen |
| ethoxythiocarbonylthio | hydrogen | hydrogen |
| dimethylamino | chloro | amino |
| amino | chloro | amino |
| acylamino | chloro | acylamino |
| hydrogen | chloro | amino |
| amino | chloro | hydrogen |
| acylamino | chloro | hydrogen |
| monoalkyl amino | chloro | amino |
| nitro | chloro | amino | and

General Formula (III)

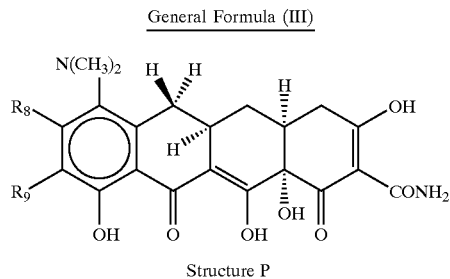

Structure P wherein R8 is hydrogen or halogen and R9 is selected from the group consisting of nitro, (N,N-dimethyl)glycylamino, and ethoxythiocarbonylthio; and

General Formula (IV)

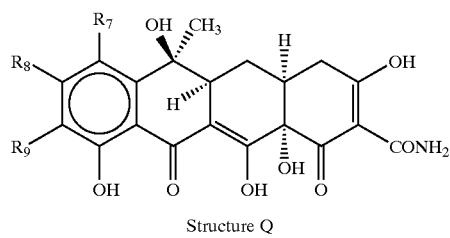

Structure Q

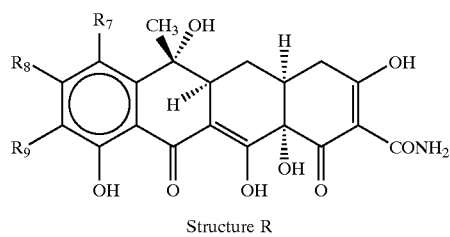

Structure R wherein R7, R8, and R9 taken together in each case, have the following meanings:

| R7 | R8 | R9 |
|---|---|---|
| amino | hydrogen | hydrogen |
| nitro | hydrogen | hydrogen |
| azido | hydrogen | hydrogen |
| dimethylamino | hydrogen | azido |
| hydrogen | hydrogen | amino |
| hydrogen | hydrogen | azido |
| hydrogen | hydrogen | nitro |
| bromo | hydrogen | hydrogen |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| diethylamino | hydrogen | hydrogen |
| hydrogen | hydrogen | ethoxythiocarbonylthio |
| dimethylamino | hydrogen | methylamino |
| dimethylamino | hydrogen | acylamino |
| dimethylamino | chloro | amino |
| amino | chloro | amino |
| acylamino | chloro | acylamino |
| hydrogen | chloro | amino |
| amino | chloro | hydrogen |
| acylamino | chloro | hydrogen |
| monoalkylamino | chloro | amino |
| nitro | chloro | amino | and pharmaceutically acceptable and unacceptable salts thereof.

In yet another embodiment, the invention provides a tetracycline compound of the formulae:

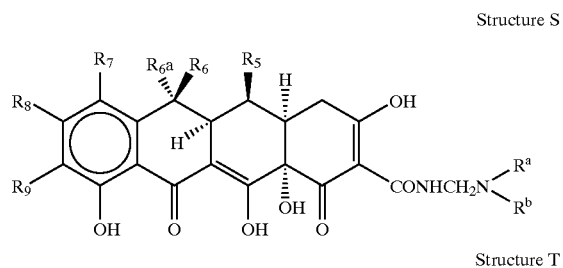

Structure S

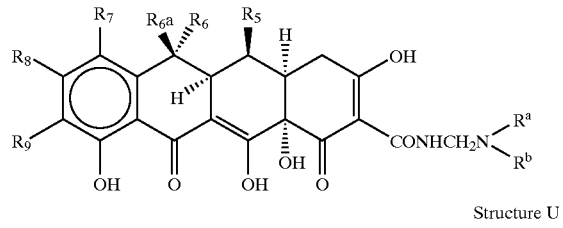

Structure T

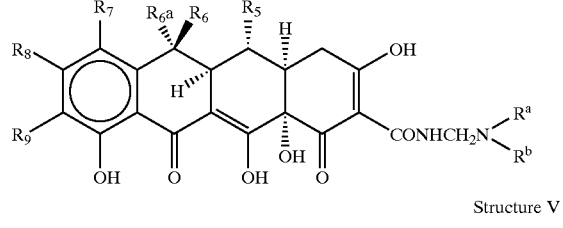

Structure U

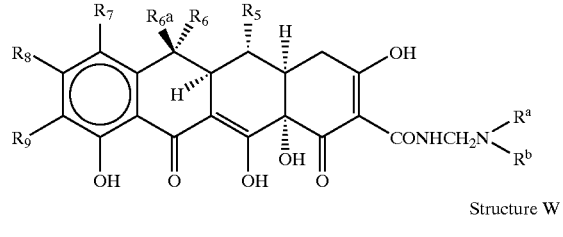

Structure V

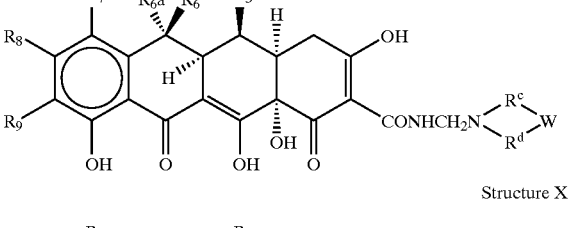

Structure W

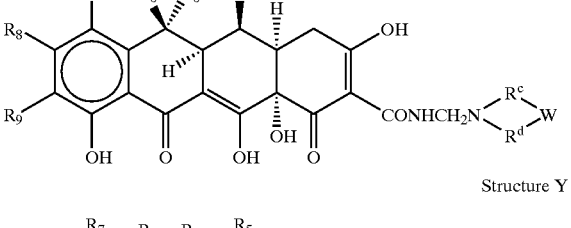

Structure X

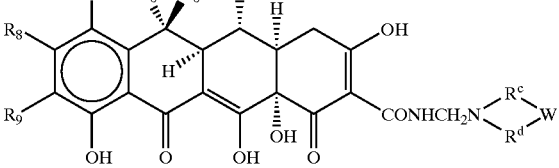

Structure Y

-continued

Structure Z

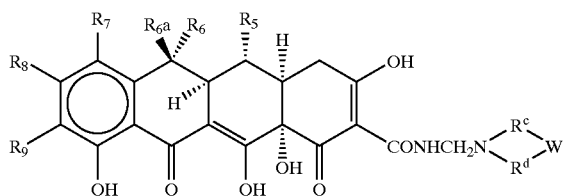

wherein R7 is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, diazonium, di(lower alkyl)amino and $RCH(NH_2)CO$; R is hydrogen or lower alkyl; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently $(CH_2)_n CHR^e$ wherein n is 0 or 1 and $R^e$ is selected from the group consisting of hydrogen, alkyl, hydroxy, lower($C_1$–$C_3$) alkoxy, amino, or nitro; and, W is selected from the group consisting of $(CHR^e)_m$ wherein m is 0–3 and $R^e$ is as above, NH, N($C_1$–$C_3$) straight chained or branched alkyl, O, S and N($C_1$–$C_4$) straight chain or branched alkoxy; and pharmaceutically acceptable and unacceptable salts thereof.

In a further embodiment, the following provisos apply: when either R7 and R9 are hydrogen then R8 must be halogen; and when R6-a, R6, R5 and R9 are all hydrogen and R7 is hydrogen, amino, nitro, halogen, dimethylamino or diethylamino, then R8 must be halogen; and when R6-a is methyl, R6 and R9 are both hydrogen, R5 is hydroxyl, and R7 is hydrogen, amino, nitro, halogen or diethylamino, then R8 is halogen; and when R6-a is methyl, R6 is hydroxyl, R5, R7 and R9 are all hydrogen, then R8 must be halogen; and when R6-a, R6 and R5 are all hydrogen, R9 is methylamino and R7 is dimethylamino, then R8 must be halogen; and when R6-a is methyl, R6 is hydrogen, R5 is hydroxyl, R9 is methylamino and R7 is dimethylamino, then R8 must be halogen; and when R6-a is methyl, R6, R5 and R9 are all hydrogen and R7 is cyano, then R8 must be halogen.

In another embodiment, the tetracycline compounds described above and below preferably have a PIF value from about 1 to about 2, more preferably at about 1. Some examples of tetracycline compounds having a PIF value of about 1 include:

STRUCTURE K
wherein: R7, R8, and R9 taken together in each case, have the following meanings:

| R7 | R8 | R9 |
|---|---|---|
| hydrogen | hydrogen | amino |
| hydrogen | hydrogen | palmitamide | and
STRUCTURE L STRUCTURE M STRUCTURE N STRUCTURE O
wherein: R7, R8, and R9 taken together in each case, have the following meanings:

| R7 | R8 | R9 |
|---|---|---|
| hydrogen | hydrogen | acetamido |
| hydrogen | hydrogen | dimethylaminoacetamido |
| hydrogen | hydrogen | nitro |
| hydrogen | hydrogen | amino | and
STRUCTURE P
wherein: R8, and R9 are, respectively, hydrogen and nitro.
Some examples of tetracycline compounds having a PIF value from about 1 to about 2 have the general formula:
STRUCTURE K:
wherein: R7, R8, and R9 taken together are, respectively, hydrogen, hydrogen and dimethylamino.

In another embodiment, the present invention provides a tetracycline compound of the formulae:
STRUCTURE C STRUCTURE D STRUCTURE E STRUCTURE F
wherein R7 is selected from the group consisting of aryl, alkenyl and alkynyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, diazonium, di(lower alkyl)amino and $RCH(NH_2)CO$; and pharmaceutically acceptable and unacceptable salts thereof; or
STRUCTURE C STRUCTURE D STRUCTURE E STRUCTURE F
wherein: R7 is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of an aryl, alkenyl and alkynyl; and pharmaceutically acceptable and unacceptable salts thereof; or
STRUCTURE C STRUCTURE D STRUCTURE E STRUCTURE F
wherein: R7 and R9 are selected from the group consisting of an aryl, alkenyl alkynyl, or mixures thereof, R6-a is selected from the group consisting of hydrogen and methyl; R6 and R5 are selected from the group consisting of hydrogen and hydroxyl; R8 is selected from the group consisting of hydrogen and halogen; and pharmaceutically acceptable and unacceptable salts thereof.

In another embodiment, the invention provides a tetracycline compound of the formulae:
STRUCTURE G STRUCTURE H STRUCTURE I STRUCTURE J
wherein R7 is selected from the group consisting of an aryl, alkenyl and alkynyl; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, di(lower alkyl)amino and RCH(NH$_2$)CO; and pharmaceutically acceptable and unacceptable salts thereof; or

STRUCTURE G STRUCTURE H STRUCTURE I STRUCTURE J wherein R7 is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; R8 is selected from the group consisting of hydrogen and halogen; R9 is selected from the group consisting of an aryl, alkenyl and alkynyl; and pharmaceutically acceptable and unacceptable salts thereof, or

STRUCTURE G STRUCTURE H STRUCTURE I STRUCTURE J wherein: R7 and R9 are selected from the group consisting of an aryl, alkenyl, alkynyl; or mixtures thereof; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; and R8 is selected from the group consisting of hydrogen and halogen; and pharmaceutically acceptable and unacceptable salts thereof;

In another embodiment, the invention provides a tetracycline compound of the formulae:

STRUCTURE K wherein R7 is selected from the group consisting of an aryl, alkenyl and alkynyl; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, di(lower alkyl)amino and RCH(NH$_2$)CO; and pharmaceutically acceptable and unacceptable salts thereof; or

STRUCTURE K wherein: R7 is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof; or

STRUCTURE K wherein: R7 and R9 are selected from the group consisting of an aryl, alkenyl, alkynyl and mixtures thereof; and R8 is selected from the group consisting of hydrogen and halogen; and pharmaceutically acceptable and unacceptable salts thereof; and

STRUCTURE L STRUCTURE M STRUCTURE N STRUCTURE O wherein: R7 is selected from the group consisting of an aryl, alkenyl and alkynyl; R8 is selected from the group consisting of hydrogen and halogen; and pharmaceutically acceptable and unacceptable salts thereof; or

STRUCTURE L STRUCTURE M STRUCTURE N STRUCTURE O wherein R7 is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof; or

STRUCTURE L STRUCTURE M STRUCTURE N STRUCTURE O wherein R7 is and R9 are selected from the group consisting of an aryl, alkenyl, alkynyl and mixtures thereof; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, di(lower alkyl)amino and RCH(NH$_2$)CO; and pharmaceutically acceptable and unacceptable salts thereof; and

STRUCTURE P wherein R9 is selected from the group consisting of an aryl, alkenyl and alkynyl; and R8 is selected from the group consisting of hydrogen and halogen; and pharmaceutically acceptable and unacceptable salts thereof; and

STRUCTURE Q STRUCTURE R wherein R7 is selected from the group consisting of an aryl, alkenyl and alkynyl; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, di(lower alkyl)amino and RCH(NH$_2$)CO; and pharmaceutically acceptable and unacceptable salts thereof; or

STRUCTURE Q STRUCTURE R wherein R7 is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof; or

STRUCTURE Q STRUCTURE R wherein R7 and R9 are selected from the group consisting of an aryl, alkenyl, alkynyl; and mixtures thereof; R8 is selected from the group consisting of hydrogen and halogen; and pharmaceutically acceptable and unacceptable salts thereof.

In another embodiment, the invention provides a tetracycline compound of the formulae:

STRUCTURES S–Z wherein R7 is selected from the group consisting of an aryl, alkenyl and alkynyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, diazonium, di(lower alkyl)amino and RCH(NH$_2$)CO; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_n CHR^e$ wherein n is 0 or 1 and $R^e$ is selected from the group consisting of hydrogen, alkyl, hydroxy, lower($C_1$–$C_3$) alkoxy, amino, or nitro; and, W is selected from the group consisting of $(CHR^e)_m$ wherein m is 0–3 and said $R^e$ is as above, NH, N($C_1$–$C_3$) straight chained or branched alkyl, O, S and N($C_1$–$C_4$) straight chain or branched alkoxy; and pharmaceutically acceptable and unacceptable salts thereof; or

STRUCTURES S–Z wherein R7 is selected from the group consisting of hydrogen, amino, nitro, mono(lower alkyl) amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of an aryl, alkenyl and alkynyl; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_nCHR^e$ wherein n is 0 or 1 and $R^e$ is selected from the group consisting of hydrogen, alkyl, hydroxy, lower($C_1$–$C_3$) alkoxy, amino, or nitro; and, W is selected from the group consisting of $(CHR^e)_m$ wherein m is 0–3 and said $R^e$ is as above, NH, N($C_1$–$C_3$) straight chained or branched alkyl, O, S and N($C_1$–$C_4$) straight chain or branched alkoxy; and pharmaceutically acceptable and unacceptable salts thereof; or

STRUCTURES S–Z wherein: R7 and R9 are selected from the group consisting of an aryl, alkenyl, alkynyl and mixtures thereof; R6-a is selected from the group consisting of hydrogen and methyl; R6 and R5 are selected from the group consisting of hydrogen and hydroxyl; R8 is selected from the group consisting of hydrogen and halogen; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_nCHR^e$ wherein n is 0 or 1 and $R^e$ is selected from the group consisting of hydrogen, alkyl, hydroxy, lower($C_1$–$C_3$) alkoxy, amino, or nitro; and W is selected from the group consisting of $(CHR^e)_m$ wherein m is 0–3 and said $R^e$ is as above, NH, N($C_1$–$C_3$) straight chained or branched alkyl, O, S and N($C_1$–$C_4$) straight chain or branched alkoxy; and pharmaceutically acceptable and unacceptable salts thereof.

The present invention includes a method for treating a mammal suffering from a condition that benefits from a non-antimicrobial dose of a tetracycline compound. Some examples of such conditions include those characterized by excessive collagen destruction, excessive MMP enzyme activity, excessive TNF activity, excessive nitric oxide activity, excessive IL-1 activity, excessive elastase activity, excessive loss of bone density, excessive protein degradation, excessive muscle wasting, excessive glycosylation of collagen, excessive COX-2 activity, insufficient bone protein synthesis, insufficient interleukin-10 production, or excessive phospholipase $A_2$ activity. The method for treating comprises administering to the mammal an effective amount of a tetracycline compound of the invention.

Conditions that benefit from a non-antimicrobial dose of a tetracycline compound include, but are not limited to, abdominal aortic aneurysm, ulceration of the cornea, periodontal disease, diabetes, diabetes mellitus, scleroderma, progeria, lung disease, cancer, graft versus host disease, disease of depressed bone marrow function, thrombocytopenia, prosthetic joint loosening, spondyloarthropathies, osteoporosis, Paget's disease, autoimmune disease, systemic lupus erythematosus, acute or chronic inflammatory condition, renal disease, connective tissue disease or neurological and neurodegenerative conditions.

Acute or chronic inflammatory conditions that can benefit from a non-antimicrobial dose of a tetracycline compound can be, but are not limited to, inflammatory bowel disease, arthritis, osteoarthritis, rheumatoid arthritis, pancreatitis, nephritis, glomerulonephritis, sepsis, septic shock, lipopolysaccharide endotoxin shock, multisystem organ failure or psoriasis.

The lung diseases that can benefit from a non-antimicrobial dose of a tetracycline compound can be, but are not limited to, ARDS, cystic fibrosis, emphysema or acute lung injury resulting from inhalation of toxicants.

The renal diseases that can benefit from a non-antimicrobial dose of a tetracycline compound include, but are not limited to chronic renal failure, acute renal failure, nephritis or glomerulonephritis.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

FIG. 1 shows the photoirritancy factor (PIF), also known as the photoinhibition factor, for some tetracycline compounds. For structure K, the compounds indicated are as follows:

| COL | R7 | R8 | R9 |
|---|---|---|---|
| 308 | hydrogen | hydrogen | amino |
| 311 | hydrogen | hydrogen | palmitamide |
| 306 | hydrogen | hydrogen | dimethylamino |

For structures L, M, N or O the compounds indicated are as follows:

| COL | R7 | R8 | R9 |
|---|---|---|---|
| 801 | hydrogen | hydrogen | acetamido |
| 802 | hydrogen | hydrogen | dimethylaminoacetamido |
| 804 | hydrogen | hydrogen | nitro |
| 805 | hydrogen | hydrogen | amino |

For structure P, R7 is hydrogen, R8 is hydrogen and R9 is nitro.

DETAILED DESCRIPTION OF THE INVENTION

Particularly preferred compounds of the present invention have D ring substituents at the 7 and/or 9 positions on the 4-dedimethylaminotetracycline molecule. These compounds include 7-azido-6-demethyl-6-deoxy-4-dedimethylamino tetracycline, 7-dimethylamino-9-azido-6-demethyl-6-deoxy-4-dedimethylamino tetracycline, 9-amino-6-demethyl-6-deoxy-4-dedimethylaminotetracycline, 9-azido-6-demethyl-6-deoxy-4-dedimethylaminotetracycline, 9-nitro-6-demethyl-6-deoxy-4-dedimethylaminotetracycline, 9-amino-7-dimethylamino-6-demethyl-6-deoxy-4-dedimethylaminotetracycline, 7-acetamido-6-demethyl-6-deoxy-4-dedimethylamino tetracycline, 9-acetamido-6-demethyl-6-deoxy-4-dedimethylaminotetracycline, 7-amino-9-nitro-6-demethyl-6-deoxy-4-dedimethylaminotetracycline, 9-(N,N,-dimethyl)glycylamino-6-demethyl-6-deoxy-4-dedimethylaminotetracycline, 7,9-diamino-6- demethyl-6-deoxy-4-dedimethylaminotetracycline, 9-ethoxythiocarbonylthio-6-demethyl-6-deoxy-4-dedimethylaminotetracycline, 7-dimethylamino-9-acetamido-6-demethyl-6-deoxy-4-dedimethylaminotetracycline, 9-azido-7-dimethylamino-6-demethyl-6-deoxy-4-dedimethylaminotetracycline, 9-azido-7-dimethylamino-6-demethyl-6-deoxy-4-dedimethylaminotetracycline, 7-azido-5-hydroxy-6-deoxy-4-dedimethylamino tetracycline, 7-dimethylamino-9-azido-5-hydroxy-6-deoxy-4-dedimethylamino tetracycline, 9-amino-5-hydroxy-6-deoxy-4-dedimethylaminotetracycline, 9-azido-5-hydroxy-6-deoxy-4-dedimethylaminotetracycline, 9-nitro-5-hydroxy-6-deoxy-4-dedimethylaminotetracycline, 9-amino-7-dimethylamino-5-hydroxy-6-deoxy-4-dedimethylaminotetracycline, 7-acetamido-5-hydroxy-6-deoxy-4-dedimethylamino tetracycline, 9-acetamido-5-hydroxy-6-deoxy-4-dedimethylaminotetracycline, 7-amino-9-nitro-5-hydroxy-6-deoxy-4-dedimethylaminotetracycline, 9-(N,N-dimethyl)glycylamino-5-hydroxy-6-deoxy-4-dedimethylaminotetracycline, 7,9-diamino-5-hydroxy-6-deoxy-4-dedimethylaminotetracycline, 7-dimethylamino-9-amino-5-hydroxy-6-deoxy-4-dedimethylaminotetracycline, 9-ethoxythiocarbonylthio-5-hydroxy-6-deoxy-4-dedimethylaminotetracycline, 7-dimethylamino-9-acetamido-5-hydroxy-6-deoxy-4-dedimethylaminotetracycline, 9-azido-7-dimethylamino-5-hydroxy-6-deoxy-4-dedimethylaminotetracycline, 9-amino-8-chloro-5-hydroxy-6-deoxy-4-dedimethylaminotetracycline, 9-(N,N-dimethyl) glycylamino-5-hydroxy-6-deoxy-4-dedimethylaminotetracycline, 9-nitro-7-dimethylamino-6-demethyl-6-deoxy-4-dedimethylaminotetracycline, 9-acetamido-7-dimethylamino-6-demethyl-6-deoxy-4-dedimethylaminotetracycline, 9-(N,N-dimethyl)glycylamino-7-dimethylamino-6-demethyl-6-deoxy-4-dedimethylaminotetracycline, and 9-ethoxythiocarbonylthio-7-dimethylamino-6-demethyl-6-deoxy-4-dedimethylaminotetracycline.

In addition, the D ring may be halogenated at the C8 position to provide 8-halodedimethylaminotetracycline derivatives. As used in this specification, halogens can be chlorine, fluorine, bromine, and iodine. Some examples of 8-halo-dedimethylaminotetracycline derivatives are 9-amino-8-chloro-7-dimethylamino-6-demethyl-6-deoxy-4-dedimethylaminotetyracycline, 9-amino-8-chloro-7-dimethylamino-5-hydroxy-6-deoxy-4-dedimethylaminotetracycline and 9-amino-8-chloro-6-demethyl-6-deoxy-4-dedimethylaminotetracycline.

In one embodiment of the invention, the 4-dedimethylaminotetracycline derivatives are substituted with an oxime, NH-alkyl, or N—NH-alkyl group at the C4 position. These compounds have the general formula:

STRUCTURE G STRUCTURE H STRUCTURE I STRUCTURE J wherein R7 is selected from the group consisting of hydrogen, amino, nitro, mono(lower alkyl) amino, halogen, and di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; R8 is selected from the group consisting of hydrogen and halogen; R9 is selected from the group consisting of hydrogen, amino, azido, nitro, acylamino, hydroxy, ethoxythiocarbonylthio, mono(lower alkyl) amino, halogen, di(lower alkyl)amino and RCH(NH$_2$)CO; R is hydrogen or lower alkyl; and pharmaceutically acceptable and unacceptable salts thereof; with the following provisos: when R4 is NOH, N—NH-alkyl or NH-alkyl and R7, R6-a, R6, R5, and R9 are all hydrogen, then R8 must be halogen; and when R4 is NOH, R6-a is methyl, R6 is hydrogen or hydroxyl, R7 is halogen, R5 and R9 are both hydrogen, then R8 must be halogen; and when R4 is N—NH-alkyl, R6-a is methyl, R6 is hydroxyl and R7, R5, R9 are all hydrogen, then R8 must be halogen; and when R4 is NH-alkyl, R6-a, R6, R5 and R9 are all hydrogen, R7 is hydrogen, amino, mono(lower alkyl)amino, halogen, di(lower alkyl)amino or hydroxyl, then R8 must be halogen; and when R4 is NH-alkyl, R6-a is methyl, R6 and R9 are both hydrogen, R5 is hydroxyl, and R7 is mono(lower alkyl)amino or di(lower alkyl)amino, then R8 must be halogen; and when R4 is NH-alkyl, R6-a is methyl, R6 is hydroxy or hydrogen and R7, R5, and R9 are all be hydrogen, then R8 must be halogen.

It will be understood that if the stereochemistry of a substituent on rings A–D of the novel 4-dedimethylaminotetracycline derivative is not specified, then both epimers are intended to be encompassed.

As used herein, NH-Alkyl, N—NH-Alkyl, alkoxy and alkyl groups contain straight or branched, saturated or unsaturated alkyl carbon chains, having from one to twenty-six carbon atoms. For example, alkyl groups include fatty alkyls which contain ten to twenty-six carbon atoms. Some examples of saturated fatty alkyl groups include, lauryl, myristyl, palmityl, stearyl, etc. Some examples of unsaturated fatty alkyl groups include palmitoleyl, oleyl, linoleyl, linolenyl, etc.

Alkyl groups also include lower alkyls which include straight or branched, saturated or unsaturated carbon chains, having from one to six carbon atoms. Some examples of lower alkyl groups are methyl, ethyl, propyl, butyl, isobutyl, n-butyl, secondary butyl, tertiary butyl, n-pentyl and benzyl. The alkyl moiety of acyl groups is defined as above. Some examples of acyl groups include acetyl, propionyl, butyryl, and acyl groups comprising fatty acids such as those described above.

Preferred oxime compounds include 7-azido-6-demethyl-6-deoxy-4-dedimethylamino-4-oximinotetracycline, 7-dimethylamino-9-azido-6-demethyl-6-deoxy-4-dedimethylamino-4-oximinotetracycline, 9-amino-6-demethyl-6-deoxy-4-dedimethylamino-4-oximinotetracycline, 9-azido-6-demethyl-6-deoxy-4-dedimethylamino-4-oximinotetracycline, 9-nitro-6-demethyl-6-deoxy-4-dedimethylamino-4-oximinotetracycline, 9-amino-7-dimethylamino-6-demethyl-6-deoxy-4-dedimethylamino-4-oximinotetracycline, 7-acetamido-6-demethyl-6-deoxy-4-dedimethylamino-4-oximinotetracycline, 9-acetamido-6-demethyl-6-deoxy-4-dedimethylamino-4-oximinotetracycline, 7-amino-9-nitro-6-demethyl-6-deoxy-4-dedimethylamino-4-oximinotetracycline, 9-(N,N,-dimethyl)glycylamino-6-demethyl-6-deoxy-4-dedimethylamino-4-oximinotetracycline, 7,9-diamino-6-demethyl-6-deoxy-4-dedimethylamino-4-oximinotetracycline, 9-ethoxythiocarbonylthio-6-demethyl-6-deoxy-4-dedimethylamino-4-oximinotetracycline, 7-dimethylamino-9-acetamido-6-demethyl-6-deoxy-4-dedimethylamino-4-oximinotetracycline, 9-azido-7-dimethylamino-6-demethyl-6-deoxy-4-dedimethylamino-4-oximinotetracycline, 9-azido-7-dimethylamino-6-demethyl-6-deoxy-4-dedimethylamino-4-oximinotetracycline, 7-azido-5-hydroxy-6-deoxy-4-dedimethylamino-4-oximinotetracycline, 7-dimethylamino-9-azido-5-hydroxy-6-deoxy-4-dedimethylamino-4-oximino-tetracycline, 9-amino-5-hydroxy-6-deoxy-4- dedimethylamino-4-oximinotetracycline, 9-azido-5-hydroxy-6-deoxy-4-dedimethylamino-4-oximinotetracycline, 9-nitro-5-hydroxy-6-deoxy-4-dedimethylamino-4-oximinotetracycline, 9-amino-7-dimethylamino-5-hydroxy-6-deoxy-4-dedimethylamino-4-oximinotetracycline, 7-acetamido-5-hydroxy-6-deoxy-4-dedimethylamino-4-oximinotetracycline, 9-acetamido-5-hydroxy-6-deoxy-4-dedimethylamino-4-oximinotetracycline, 7-amino-9-nitro-5-hydroxy-6-deoxy-4-dedimethylamino-4-oximinotetracycline, 9-(N,N-dimethyl)glycylamino-5-hydroxy-6-deoxy-4-dedimethylamino-4-oximinotetracycline, also known as 9-dimethylaminoacetamido-5-hydroxy-6-deoxy-4-dedimethylamino-4-oximinotetracycline, 7,9-diamino-5-hydroxy-6-deoxy-4-dedimethylamino-4-oximinotetracycline, 7-dimethylamino-9-amino-5-hydroxy-6-deoxy-4-dedimethylamino-4-oximinotetracycline, 9-ethoxythiocarbonylthio-5-hydroxy-6-deoxy-4-dedimethylamino-4-oximinotetracycline, 7-dimethylamino-9-acetamido-5-hydroxy-6-deoxy-4-dedimethylamino-4-oximinotetracycline, 9-azido-7-dimethylamino-5-hydroxy-6-deoxy-4-dedimethylamino-4-oximinotetracycline, 9-amino-8-chloro-5-hydroxy-6-deoxy-4-dedimethylamino-4-oximinotetracycline, 9-(N,N-dimethyl) glycylamino-5-hydroxy-6-deoxy-4-dedimethylamino-4-oximinotetracycline, 9-nitro-7-dimethylamino-6-demethyl-6-deoxy-4-dedimethylamino-4-oximinotetracycline, 9-acetamido-7-dimethylamino-6-demethyl-6-deoxy-4-dedimethylamino-4-oximino-tetracycline, 9-(N,N-dimethyl) glycylamino-7-dimethylamino-6-demethyl-6-deoxy-4-dedimethylamino-4-oximino-tetracycline, and 9-ethoxythiocarbonylthio-7-dimethylamino-6-demethyl-6-deoxy-4-dedimethylamino-4-oximinotetracycline.

In addition, the D ring may be halogenated at the C8 position to provide 8-halo-4-dedimethylamino-4-oximinotetracycline compounds. Some examples include 9-amino-8-chloro-7-dimethylamino-6-demethyl-6-deoxy-4-dedimethylamino-4-oximinotetracycline, 9-amino-8-chloro-7-dimethylamino-5-hydroxy-6-deoxy-4-dedimethylamino-4-oximinotetracycline and 9-amino-8-chloro-6-demethyl-6-deoxy-4-dedimethylamino-4-oximinotetracycline.

Preferred hydrazone compounds include 7-azido-6-demethyl-6-deoxy-4-dedimethylaminotetracycline-4-methyl or ethyl hydrazone, 7-dimethylamino-9-azido-6-demethyl-6-deoxy-4-dedimethylaminotetracycline-4-methyl or ethyl hydrazone, 9-amino-6-demethyl-6-deoxy-4-dedimethylaminotetracycline-4-methyl or ethyl hydrazone, 9-azido-6-demethyl-6-deoxy-4-dedimethylaminotetracycline-4-methyl or ethyl hydrazone, 9-nitro-6-demethyl-6-deoxy-4-dedimethylaminotetracycline-4-methyl or ethyl hydrazone, 9-amino-7-dimethylamino-6-demethyl-6-deoxy-4-dedimethylaminotetracycline-4-methyl or ethyl hydrazone, 7-acetamido-6-demethyl-6-deoxy-4-dedimethylaminotetracycline-4-methyl or ethyl hydrazone, 9-acetamido-6-demethyl-6-deoxy-4-dedimethylaminotetracycline-4-methyl or ethyl hydrazone, 7-amino-9-nitro-6-demethyl-6-deoxy-4-dedimethylaminotetracycline-4-methyl or ethyl hydrazone, 9-(N,N,-dimethyl)glycylamino-6-demethyl-6-deoxy-4-dedimethylaminotetracycline-4-methyl or ethyl hydrazone, 7,9-diamino-6-demethyl-6-deoxy-4-dedimethylaminotetracycline-4-methyl or ethyl hydrazone, 9-ethoxythiocarbonylthio-6-demethyl-6-deoxy-4-dedimethylaminotetracycline-4-methyl or ethyl hydrazone, 7-dimethylamino-9-acetamido-6-demethyl-6-deoxy-4-dedimethylaminotetracycline-4-methyl or ethyl hydrazone, 9-azido-7-dimethylamino-6-demethyl-6-deoxy-4-dedimethylamino tetracycline-4-methyl or ethyl hydrazone, 9-azido-7-dimethylamino-6-demethyl-6-deoxy-4-dedimethylaminotetracycline-4-methyl or ethyl hydrazone, 7-azido-5-hydroxy-6-deoxy-4-dedimethylaminotetracycline-4-methyl or ethyl hydrazone, 7-dimethylamino-9-azido-5-hydroxy-6-deoxy-4-dedimethylaminotetracycline-4-methyl or ethyl hydrazone, 9-amino-5-hydroxy-6-deoxy-4-dedimethylaminotetracycline-4-methyl or ethyl hydrazone, 9-azido-5-hydroxy-6-deoxy-4-dedimethylaminotetracycline-4-methyl or ethyl hydrazone, 9-nitro-5-hydroxy-6-deoxy-4-dedimethylamino tetracycline-4-methyl or ethyl hydrazone, 9-amino-7-dimethylamino-5-hydroxy-6-deoxy-4-dedimethylaminotetracycline-4-methyl or ethyl hydrazone, 7-acetamido-5-hydroxy-6-deoxy-4-dedimethylaminotetracycline-4-methyl or ethyl hydrazone, 9-acetamido-5-hydroxy-6-deoxy-4-dedimethylaminotetracycline-4-methyl or ethyl hydrazone, 7-amino-9-nitro-5-hydroxy-6-deoxy-4-dedimethylaminotetracycline-4-methyl or ethyl hydrazone, 9-(N,N-dimethyl) glycylamino-5-hydroxy-6-deoxy-4-dedimethylaminotetracycline-4-methyl or ethyl hydrazone, 7,9-diamino-5-hydroxy-6-deoxy-4-dedimethylaminotetracycline-4-methyl or ethyl hydrazone, 7-dimethylamino-9-amino-5-hydroxy-6-deoxy-4-dedimethylaminotetracycline-4-methyl or ethyl hydrazone, 9-ethoxythiocarbonylthio-5-hydroxy-6-deoxy-4-dedimethylaminotetracycline-4-methyl or ethyl hydrazone, 7-dimethylamino-9-acetamido-5-hydroxy-6-deoxy-4-dedimethylaminotetracycline-4-methyl or ethyl hydrazone, 9-azido-7-dimethylamino-5-hydroxy-6-deoxy-4-dedimethylaminotetracycline-4-methyl or ethyl hydrazone, 9-amino-8-chloro-5-hydroxy-6-deoxy-4-dedimethylaminotetracycline-4-methyl or ethyl hydrazone, 9-(N,N-dimethyl) glycylamino-5-hydroxy-6-deoxy-4-dedimethylamino tetracycline-4-methyl or ethyl hydrazone, 9-nitro-7-dimethylamino-6-demethyl-6-deoxy-4-dedimethylaminotetracycline-4-methyl or ethyl hydrazone, 9-acetamido-7-dimethylamino-6-demethyl-6-deoxy-4-dedimethylaminotetracycline-4-methyl or ethyl hydrazone, 9-(N,N-dimethyl) glycylamino-7-dimethylamino-6-demethyl-6-deoxy-4-dedimethylaminotetracycline-4-methyl or ethyl hydrazone, and 9-ethoxythiocarbonylthio-7-dimethylamino-6-demethyl-6-deoxy-4-dedimethylaminotetracycline-4-methyl or ethyl hydrazone.

The D ring may be halogenated at the C8 position to provide 8-halo-4-dedimethylaminotetracycline-4-hydrazone compounds. Some examples include 9-amino-8-chloro-7-dimethylamino-6-demethyl-6-deoxy-4-dedimethylamino tetracycline-4-methyl or ethyl hydrazone, 9-amino-8-chloro-7-dimethylamino-5-hydroxy-6-deoxy-4-dedimethylamino tetracycline-4-methyl or ethyl hydrazone and 9-amino-8-chloro-6-demethyl-6-deoxy-4-dedimethylaminotetracycline-4-methyl or ethyl hydrazone.

Novel 4-dedimethlyaminotetracycline derivatives of the present invention also include compounds with an NH-Alkyl (alkylamino) substituent at the C4 position on the A ring. These compounds have substitutions at the C5, C6, C6a, C7, C8 and/or C9 positions as described above. An example is 9-azido-8-chloro-7-dimethylamino-5-hydroxy-6-deoxy-4-dedimethylaminotetracycline.

In addition, a hexanoylamino group can be added to the C9 position on the D ring of any compound of the invention. An example includes, but is not limited to, 4-dedimethylamino-6-demethyl-6-deoxy-9-hexanoylaminotetracycline.

In another embodiment of the invention, the 4-dedimethylaminotetracycline derivatives are Mannich derivatives of the compounds described above. Such derivatives include, for example, compounds having the general formula:

STRUCTURE S STRUCTURE T STRUCTURE U STRUCTURE V
STRUCTURE W STRUCTURE X STRUCTURE Y STRUCTURE Z wherein R5, R6, R7, R8 and R9 are as described above; $R^a$ and $R^b$ are selected from the group consisting of hydrogen, methyl, ethyl, n-propyl or 1-methylethyl with the proviso that $R^a$ and $R^b$ cannot both be hydrogen; $R^c$ and $R^d$ are, independently, $(CH_2)_n CHR^e$ wherein n is 0 or 1 and $R^e$ is selected from the group consisting of hydrogen, alkyl, hydroxy, lower($C_1$–$C_3$) alkoxy, amino, or nitro; and, W is selected from the group consisting of $(CHR^e)_m$ wherein m is 0–3 and $R^e$ is as above, NH, N($C_1$–$C_3$) straight chained or branched alkyl, O, S and N($C_1$–$C_4$) straight chain or branched alkoxy; and pharmaceutically acceptable and unacceptable salts thereof. For example, when m is 0, $R^c$ and $R^d$ are bonded to each other in a 3–5 membered ring, such as, for example, a pyrrolidino or substituted pyrrolidino ring, a morpholino or substituted morpholino ring, or a piperazino or substituted piperazino ring.

These Mannich derivatives include, for example, compounds with a piperazin-1-yl, 4-methylpiperazin-1-yl, morpholin-1-yl, or pyrrolidin-1-yl substituent at the C2 position. These compounds have substituents at the C4, C5, C6, C6a, C7, C8 and/or C9 positions as described above. Examples of such compounds include, but are not limited to, N-morpholin-1-ylmethyl-4-dedimethylamino-6-demethyl-6-deoxytetracyline, N-pyrrolidin-1-ylmethyl-4-dedimethylamino-6-demethyl-6-deoxytetracyline, N-morpholin-1-ylmethyl-4-dedimethylamino-6-demethyl-6-deoxy-9-hexanoylaminotertracycline, N-pyrrolidin-1-ylmethyl-4-dedimethylamino-6-demethyl-6-deoxy-9-hexanoylaminotetracycline.

In another embodiment of the invention, the 4-dedimethylaminotetracycline derivatives are substituted at the C7 or C9 position, or at both the C7 and C9 positions, with an aryl, alkenyl, or alkynyl group, or mixtures thereof. Such compounds include, for example, compounds having any of the general formulas C–Z wherein R4, R5, R6, R6a, R8, Ra, Rb, Rc, Rd and W are as described above; with the provisos that when R7 is not an aryl, alkenyl or alkynyl group, R7 is a hydrogen, amino, nitro, mono(lower alkyl) amino, halogen, di(lower alkyl)amino, ethoxythiocarbonylthio, azido, acylamino, diazonium, cyano, or hydroxyl; and when R9 is not an aryl, alkenyl or alkynyl group, R9 is hydrogen, amino, azido, nitro, acylamino, hydroxy, ethoxythiocarbonylthio, mono(lower alkyl)amino, halogen, di(lower alkyl)amino or $RCH(NH_2)CO$.

In this specification, an aryl group is any monocyclic or polycyclic aromatic group derived from an aromatic compound. The most typical example of a monocyclic aromatic compound is benzene and substituted benzene derivatives. Examples of polycyclic aromatic compounds include, but are not limited to, naphthalene, anthracene, 1,2-benzylpyrene, and coronene.

The alkenyl, and alkynyl groups at either or both of the C7 or C9 positions include any of the alkyl groups described herein, further having, respectively, one or more double or triple bonds, preferably one to three double or triple bonds, at any position. Some examples of alkenyl groups include, but are not limited to, ethylenyl, propenyl, 1-butylenyl, 2-butylenyl and 2-methylpropylenyl and 1,3 hexadienyl. The alkynyl groups include, but are not limited to, ethynyl, propynyl, 1-butynyl, 2-butynyl and 2-methylpropynyl and 1,3 hexadiynyl.

The aryl, alkenyl and alkynyl groups may be further substituted at any position with one or more additional substituents. Some examples of such further substitutions include, but are not limited to, nitro, amino, halo (F, Cl, Br or I), amido, azido, cyano, hydroxyl, alkoxy, preferably lower alkoxy, acyl, preferably lower acyl, amidoazido, mono (lower alkyl)amino, di(lower alkyl)amino, ethoxythiocarboxylthio, diazonium, acylamino, N,N-dimethylglycylamino, and alkyl groups, preferably lower alkyl groups. Examples of substituted benzene derivatives include, but are not limited to, methylbenzene (toluene), nitrobenzene, hydroxybenzene (phenol), aminobenzene (aniline), vinylbenzene (styrene), benzaldehyde, benzoic acid, 1,2-dimethylbenzene (ortho-xylene), 1,3 dimethylbenzene (meta-xylene), and 1,4-dimethylbenzene (para-xylene).

Some examples of compounds having aryl substituents at the C7 or C9 positions include 7-phenyl-6-demethyl-6-deoxy-4-dedimethylaminotetracycline, 9-phenyl-6-demethyl-6-deoxy-4-dedimethylaminotetracycline, 7-(4-fluorophenyl)-6-demethyl-6-deoxy-4-dedimethylaminotetracycline, 9-(4-fluorphenyl)-6-demethyl-6-deoxy-4-dedimethylaminotetracycline, 7-(4-chlorophenyl)-6-demethyl-6-deoxy-4-dedimethylaminotetracycline, 9-(4-chlorophenyl)-6-demethyl-6-deoxy-4-dedimethylaminotetracycline, 7-(4-nitrophenyl)-6-demethyl-6-deoxy-4-dedimethylaminotetracycline, 9-(4-nitrophenyl)-6-demethyl-6-deoxy-4-dedimethylaminotetracycline, 7-(4-dimethylamino)-6-demethyl-6-deoxy-4-dedimethylaminotetracycline, 9-(4-dimethylamino)-6-demethyl-6-deoxy-4-dedimethylaminotetracycline, 7-phenyl-5-hydroxy-6-deoxy-4-dedimethyaminotetracycline, 9-phenyl-5-hydroxy-6-deoxy-4-dedimethylaminotetracycline, 7-(4-fluorophenyl)-5-hydroxy-6-deoxy-4-dedimethyaminotetracycline, 9-(4-fluorphenyl)-5-hydroxy-6-deoxy-4-dedimethyaminotetracycline, 7-(4-chlorophenyl)-5-hydroxy-6-deoxy-4-dedimethyaminotetracycline, 9-(4-chlorophenyl)-5-hydroxy-6-deoxy-4-dedimethyaminotetracycline, 7-(4-nitrophenyl)-5-hydroxy-6-deoxy-4-dedimethyaminotetracycline, 9-(4-nitrophenyl)-5-hydroxy-6-deoxy-4-dedimethyaminotetracycline, 7-(4-dimethylamino)-5-hydroxy-6-deoxy-4-dedimethyaminotetracycline, 9-(4-dimethylamino)-5-hydroxy-6-deoxy-4-dedimethyaminotetracycline, 7-phenyl-7-dimethylamino-4-dedimethylaminotetracycline, 9-phenyl-7-dimethylamino-4-dedimethylaminotetracycline, 7-(4-fluorophenyl)-7-dimethylamino, 4-dedimethylaminotetracycline, 9-(4-fluorphenyl)-7-dimethylamino-4-dedimethylaminotetracycline, 7-(4-chlorophenyl)-7-dimethylamino-4-dedimethylaminotetracycline, 9-(4-chlorophenyl)-7-dimethylamino-4-dedimethylaminotetracycline, 7-(4-nitrophenyl)-7-dimethylamino-4-dedimethylaminotetracycline, 9-(4-nitrophenyl)-7-dimethylamino-4-dedimethylaminotetracycline, 7-(4-dimethylamino)-7-dimethylamino-4-dedimethylaminotetracycline, 9-(4-dimethylamino)-7-dimethylamino-4-dedimethylaminotetracycline, 7-phenyl-4-dedimethylaminotetracycline, 9-phenyl-4-dedimethylaminotetracycline, 7-(4-fluorophenyl)-4-dedimethylaminotetracycline, 9-(4-fluorphenyl)-4-dedimethylaminotetracycline, 7-(4-chlorophenyl)-4-dedimethylaminotetracycline, 9-(4-chlorophenyl)-4-dedimethylaminotetracycline, 7-(4-nitrophenyl)-4-dedimethylaminotetracycline, 9-(4-nitrophenyl)-4-dedimethylaminotetracycline, 7-(4-dimethylamino)-4-dedimethylaminotetracycline, 9-(4-dimethylamino)-4-dedimethylaminotetracycline.

Some examples of compounds having alkenyl or alkynyl substituents at the C7 or C9 positions include the same C7 and C9 aryl substituted tetracycline derivatives described above, but instead having alkenyl or alkynyl substituents that are two to four carbons in length attached to the C7 and C9 positions. The alkenyl groups include, but are not limited to, ethenyl, propenyl, 1-butenyl, 2-butenyl and 2-methylpropenyl. The alkynyl groups include, but are not limited to, ethynyl, propynyl, 1-butynyl, 2-butynyl and 2-methylpropynyl.

The novel 4-dedimethylaminotetracycline compounds of the present invention including pharmaceutically acceptable and unacceptable salts thereof may be prepared by D ring substitution at the C7, C8 and/or C9 positions using starting reactants that can readily be prepared or purchased by methods known in the art. See, for example, Mitscher, L. A., The Chemistry of the Tetracycline Antibiotics, Marcel Dekker, New York (1978), Ch. 6, Hlavka, J. and J. H. Boothe, The Tetracyclines, Springer-Verlag, Berlin-Heidelberg, page 18 (1985) and U.S. Pat. Nos. 4,704,383, 3,226,436, 3,047,626 3,518,306 and 5,532,227.

For example, nitration of the C9 position on the D ring may be accomplished, and novel 9-nitro compounds may be prepared, by using known starting reactants such as 7-dimethylamino-6-demethyl-6-deoxy-4-dedimethylaminotetracycline or 6-deoxy-4-dedimethylaminotetracycline and treating these compounds with a strong acid and metal nitrate salts. Examples of strong acids that are suitable for use in the present invention are: sulfuric acid, trifluoroacetic acid, methanesulfonic acid or perchloric acid. Suitable metal nitrate salts are, for example, calcium, potassium or sodium nitrate. The C9 position on the D ring undergoes nitration to form the corresponding 9-nitro-7-dimethylamino-6-demethyl-6-deoxy-4-dedimethylaminotetracycline or 9-nitro-6-deoxy-4-dedimethylaminotetracycline compounds.

Amination of the C9 position on the D ring may be accomplished by treating a 9-nitro-4-dedimethylaminotetracycline, such as 9-nitro-7-dimethylamino-6-demethyl-6-deoxy-4-dedimethylaminotetracycline or 9-nitro-6-deoxy-4-dedimethylaminotetracycline with hydrogen in the presence of a suitable supported catalyst such as Raney nickel, platinum oxide or palladium-on-carbon. This is then filtered and washed with an organic solvent such as ether. The C9 substituent is reduced to form the corresponding 9-amino-7-dimethylamino-6-demethyl-6-deoxy-4-dedimethylaminotetracycline or 9-amino-6-deoxy-4-dedimethylaminotetracycline compound.

The amino group on the D ring at the C9 position may be converted to an acylamido group or a sulfonamido group. For example, 9-amino-7-dimethylamino-6-demethyl-6-deoxy-4-dedimethylaminotetracycline or 9-amino-6-deoxy-4-dedimethylaminotetracycline compounds are treated with acyl chloride, acyl anhydride, mixed acyl anhydride, sulfonyl chloride or sulfonyl anhydride in the presence of a suitable acid scavenger dispersed in a solvent. The acid scavenger is suitably selected from sodium bicarbonate, sodium acetate, pyridine, triethylamine, N,O-bis(trimethylsilyl)acetamide, N,O-bis(trimethylsilyl) trifluoroacetamide or a basic ion-exchange resin. Solvents suitable for the acylation reaction include water, water-tetrahydrofuran, N-methylpyrolidone, 1,3-dimethyl-2-imidazolidione, hexamethylphosphoramide, 1,3,dimethyl-3,4,5,6-tetrahydro-2(1H)-pyrimidinone or 1,2-dimethoxyethane. The C9 amino group may be converted to the acetamido group to form, for example, the corresponding 9-acetamido-7-dimethylamino-6-demethyl-6-deoxy-4-dedimethylamino tetracycline or 9-acetamido-6-deoxy-4-dedimethylamino tetracycline.

A diazonium group can also be substituted at the C9 position on the D-ring. Typically, a 9-amino-4-dedimethylaminotetracycline derivative, such as 9-amino-7-dimethylamino-6-demethyl-6-deoxy-4-dedimethylaminotetracycline or 9-amino-6-deoxy-4-dedimethylaminotetracycline in 0.1N HCL in methanol is treated with n-butyl nitrite to form the corresponding 9-diazonium derivatives such as 9-diazonium-7-dimethylamino-6-demethyl-6-deoxy-4-dedimethylaminotetracycline or 9-diazonium-6-deoxy-4-dedimethylaminotetracycline.

The 9-diazonium-4-dedimethylaminotetracycline derivatives, such as 9-diazonium-7-dimethylamino-6-demethyl-6-deoxy-4-dedimethylaminotetracycline or 9-diazonium-6-deoxy-4-dedimethylaminotetracycline can be treated with methanolic hydrochloric acid plus a triazo compound such as sodium azide to form, 9-azido derivatives, such as 9-azido-7-dimethylamino-6-demethyl-6-deoxy-4-dedimethylaminotetracycline or 9-azido-6-deoxy-4-dedimethylaminotetracycline.

Alternately, an ethoxythiocarbonylthio group can be substituted at the C9 position on the D ring. For example, a 9-diazonium-4-dedimethylaminotetracycline derivative, such as 9-diazonium-7-dimethylamino-6-demethyl-6-deoxy-4-dedimethylamino tetracycline or 9-diazonium-6-deoxy-4-dedimethylaminotetracycline is treated with an acid metal salt such as potassium ethyl xanthate to form the corresponding 9-ethoxythiocarbonylthio derivative, such as 9-ethoxythiocarbonylthio-7-dimethylamino-6-demethyl-6-deoxy-4-dedimethylamino or 9-ethoxythiocarbonylthio-6-deoxy-4-dedimethylaminotetracycline.

The above reactions describe substitution at the C9 position on 4-dedimethylaminotetracycline molecule. Some substitution may also occur, depending on the starting reactants and conditions used, at the C7 position and lead to also 7-substituted-4-dedimethylaminotetracycline derivatives, such as 7-diazonium-6-demethyl-6-deoxy-4-dedimethylaminotetracycline or 7-azido-6-demethyl-6-deoxy-4-dedimethylaminotetracycline. The 7-substituted derivatives can be separated from the 9-substituted derivatives, and purified as discussed below.

The novel 7 or 9 azido-4-dedimethylamino derivatives of the present invention can be halogenated at the C8 position by treating 7 or 9-azido-4-dedimethylaminotetracycline with a strong acid such as hydrogen halide, sulfuric acid saturated with hydrogen halide or methanesulfonic acid saturated with hydrogen halide. The product that is isolated, when the hydrogen halide is hydrogen chloride, is the 8-chloro (7 or 9) amino-4-dedimethylaminotetracycline derivative. A particularly preferred halogenated compound is 9-acetamido-8-chloro-7-dimethylamino-6-deoxy-6-demethyl-4-dedimethylamino tetracycline.

In one embodiment, 4-dedimethylaminotetracycline compounds of the present invention have an oxime (NOH), alkylamino (NH-alkyl), or alkylhydrazone (N—NH-alkyl) group at the C4 position on the A ring. These compounds can be made using known methods. For example, 4-hydroxytetracycloxide may be treated with hydroxyamine or ethylhydrazine under alkaline conditions in a solvent such as methanol or ethanol. Substitution at the C4 position occurs and 4-dedimethylamino-4-oximinotetracycline and 4-dedimethylaminotetracycline-4-alkylhydrazone compounds can be isolated as alkali metal salts. See for example, U.S. Pat. Nos. 3,622,627, 3,159,675 and 3,345,370. Substitution at C7, C8, and/or C9 positions on the D ring using methods previously described (i.e. halogenation, amination, or nitration) give rise to the novel 4-oxime, 4-hydrazone and 4-aminoalkyl compounds of the present invention.

The Mannich derivatives can be made by methods known in the art. For example, the tetracycline derivatives described above may be treated with formaldehyde and the appropriate amine.

Aryl, alkenyl and alkynyl groups can be added onto the C7 and C9 positions of the tetracycline derivatives described above by methods known in the art. Such methods include modified Suzuki and Stille coupling reactions. See, for example, Koza D. J., *Organic Letters,* 2000. For example, the tetracycline derivatives described above having an iodine attached to the C7or C9 positions can be treated with tri-n-butylstannyl reagent in the presence of a palladium catalyst and copper iodide. This reaction can be extended to a variety of aryl, alkenyl and alkynyl derivatives.

Examples of specific embodiments are described above as derivatives of the specific antibiotic compound tetracycline. The compounds of the invention are not, however, limited to derivatives of any specific tetracycline compound. Rather, the compounds of the invention include the 4-dedimethyl derivatives of any member of the tetracycline family. Thus, the invention also includes, but is not limited to, the same 4-dedimethylamino derivatives and 4-substituted 4-dedimethylamino derivatives of sancycline, minocycline, and doxycycline as the tetracycline derivatives mentioned above.

The present invention embraces salts, including acid-addition and metal salts, of the 4-dedimethylamino- tetracycline compounds described herein. Such salts are formed by well known procedures with both pharmaceutically acceptable and pharmaceutically unacceptable acids and metals. By "pharmaceutically acceptable" is meant those salt-forming acids and metals which do not substantially increase the toxicity of the compound.

Some examples of suitable salts include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like. The pharmaceutically unacceptable acid addition salts, while not useful for therapy, are valuable for isolation and purification of the new substances. Further, they are useful for the preparation of pharmaceutically acceptable salts. Of this group, the more common salts include those formed with hydrofluoric and perchloric acids. Hydrofluoride salts are particularly useful for the preparation of the pharmaceutically acceptable salts, e.g. the hydrochlorides, by dissolution in hydrochloric acid and crystallization of the hydrochloride salt formed. The perchloric acid salts are useful for purification and crystallization of the new products.

Whereas metal salts may, in general, be prepared and are useful for various purposes, the pharmaceutically acceptable metal salts are particularly valuable because of their utility in therapy. The pharmaceutically acceptable metals include more commonly sodium, potassium and alkaline earth metals of atomic number up to and including 20, i.e., magnesium and calcium and additionally, aluminum, zinc, iron and manganese, among others. Of course, the metal salts include complex salts, i.e. metal chelates, which are well recognized in the tetracycline art.

After preparation, the novel compounds of the present invention can be conveniently purified by standard methods known in the art. Some suitable examples include crystallization from a suitable solvent or partition-column chromatography.

The novel 4-dedimethylaminotetracycline compounds of the present invention can be used in vivo, in vitro, and ex vivo, for example, in living mammals as well as in cultured tissue, organ or cellular systems. Mammals include, for example, humans, as well as pet animals such as dogs and cats, laboratory animals, such as rats and mice, and farm animals, such as horses and cows. Tissues, as used herein, are an aggregation of similarly specialized cells which together perform certain special functions. Cultured cellular systems include any mammalian cells, such as epithelial, endothelial, red blood, and white blood cells. More particularly, human peripheral blood monocytes, synovial fibroblastoid cells, and the like.

The present invention is directed to a method for treating a mammal suffering from a condition or diseases that benefits from a non-antimicrobial dose of a tetracycline compound. These conditions or diseases are characterized by excessive collagen destruction, excessive MMP enzyme activity, excessive TNF activity, excessive nitric oxide activity, excessive IL-1 activity, excessive elastase activity, excessive loss of bone density, excessive protein degradation, excessive muscle wasting, excessive glycosylation of collagen, excessive COX-2 activity, insufficient bone protein synthesis, insufficient IL-10 (interleukin-10) production or excessive phospholipase $A_2$ activity. The method comprises administering to the mammal an effective amount of a tetracycline compound of the invention.

The term "excessive," as used herein, refers to increased activity over usual activity which leads to some pathological problem in a mammal or mammalian cells.

In vivo practice of the invention permits application in the relief or palliation of medical and veterinary diseases, conditions, and syndromes. In particular, the present invention includes a method for treating a mammal suffering from conditions or diseases including abdominal aortic aneurysm, ulceration of the cornea, periodontal disease, diabetes, diabetes mellitus, scleroderma, progeria, lung disease, cancer, graft versus host diseases, disease of depressed bone marrow function, thrombocytopenia, prosthetic joint loosening, spondyloarthropathies, osteoporosis, Paget's disease, autoimmune disease, systemic lupus erythematosus, acute or chronic inflammatory conditions, renal disease or connective tissue disease by administering an effective amount of a tetracycline compound to the mammal.

Cancerous conditions treatable by tetracycline compounds of the present invention include, but are not limited to, carcinomas, blastomas, sarcomas such as Kaposi's Sarcoma, gliomas, and the twelve major cancers: prostrate cancer, breast cancer, lung cancer, colorectal cancer, bladder cancer, non-Hodgkin's lymphoma, uterine cancer, melanoma, kidney cancer, leukemia, ovarian cancer and pancreatic cancer.

Acute or chronic inflammatory conditions treatable by tetracycline compounds of the present invention include, for example, inflammatory bowel disease, arthritis, osteoarthritis, rheumatoid arthritis, pancreatitis, nephritis, glomerulonephritis, sepsis, septic shock, lipopolysaccharide endotoxin shock, multisystem organ failure or psoriasis.

Lung diseases treatable by means of the present invention include, for example, ARDS (adult respiratory distress syndrome), cystic fibrosis, emphysema or acute lung injury resulting from inhalation of toxicants. Some examples of toxicants are acids, chemicals, industrial and military poisons, smoke and other toxic products of combustion.

The novel tetracycline compounds of the present invention can also be used to treat renal diseases. Some examples of renal diseases are chronic renal failure, acute renal failure, nephritis or glomerulonephritis.

The tetracycline compounds of the present invention can also be used to treat neurological and neurodegenerative conditions. Examples of neurological and neurodegenerative conditions include, Alzheimer's disease, Guillain-Barré Syndrome (acute febrile polyneuritis), Krabbe's disease (leukodystrophy), adrenoleukodystrophy, Parkinson's disease, Huntington's disease, multiple sclerosis, amyotrophic lateral sclerosis (Lou Gehrig's disease) and encephalopathies, including spongiform encephalopathy, such as Creutzfeldt-Jakob Disease. Other examples of spongiform encephalopathies in humans include kuru, Gerstmann-Straussler-Scheinker disease and fatal familial insomnia. Other examples of spongiform encephalopathies in mammals include bovine spongiform encephalopathy (mad cow disease), scrapie in sheep and goats, transmissible mink encephalopathy, chronic wasting disease of mule deer and elk, and feline spongiform encephalopathy.

An effective amount of a tetracycline compound as used herein is that amount effective to achieve the specified result of treating the disease or condition. Preferably, the tetracycline compound or derivative is provided in an amount which has little or no antimicrobial activity. A tetracycline compound or derivative is not effectively antimicrobial if it does not significantly prevent the growth of microbes. Accordingly, the method can beneficially employ a tetracycline derivative which has been modified chemically to reduce or eliminate its antimicrobial properties. The use of such chemically-modified tetracyclines is preferred in the present invention since they can be used at higher levels than antimicrobial tetracyclines, while avoiding certain disadvantages, such as the indiscriminate killing of beneficial microbes, and the emergence of resistant microbes, which often accompanies the use of antimicrobial or antibacterial amounts of such compounds.

The maximal dosage for a mammal is the highest dosage which does not cause undesirable or intolerable side effects. Minimal dosage is the lowest dosage where efficacy is first observed. For example, the tetracycline compound can be administered in an amount of from about 0.1 mg/kg/day to about 30 mg/kg/day, and preferably from about 1 mg/kg/day to about 18 mg/kg/day. In any event, the practitioner is guided by skill and knowledge in the field, and the present invention includes without limitation dosages which are effective to achieve the described effect.

The method involves administering or providing a tetracycline derivative in an amount which is effective for treating diseases or conditions in mammalian cells or a mammal. Administering the tetracycline derivatives can be accomplished in a variety of ways. In cultured cellular systems (in vitro), tetracycline derivatives can be administered by contacting the cells directly with an effective amount of the tetracycline derivative.

In living mammals (in vivo), tetracycline derivatives of the present invention can be administered systemically by the parenteral and enteral routes which also includes controlled release delivery systems. For example, tetracycline derivatives of the present invention can easily be administered intravenously (e.g., intravenous injection) which is a preferred route of delivery. Intravenous administration can be accomplished by mixing the tetracycline derivatives in a suitable pharmaceutical carrier (vehicle) or excipient as understood by practitioners in the art.

Oral or enteral use is also contemplated, and formulations such as tablets, capsules, pills, troches, elixirs, suspensions, syrups, wafers, chewing gum and the like can be employed to provide the tetracycline derivative.

Alternatively, delivery of the tetracycline derivative can include topical application. Accordingly, the carrier is preferably suited for topical use. Compositions deemed to be suited for such topical use include gels, salves, lotions, creams ointments and the like. The tetracycline derivative may also be incorporated with a support base or matrix or the like to provide a pre-packaged surgical or burn dressing or bandage which can be directly applied to skin. Topical application of tetracycline derivatives in amounts of up to about 25% (w/w) in a vehicle are therefore appropriate depending upon indication. More preferably, application of tetracycline derivatives in amounts of from about 0.1% to about 10% is believed to be effective in treating diseases or conditions. It is believed that these quantities do not induce significant toxicity in the subject being treated.

For example, in certain cases tetracycline compounds having only limited biodistribution may be preferred for localized activity. Topical application of these non-absorbable CMTs would be desirable in oral lesions, since the CMTs would not be absorbed to any significant degree even if swallowed.

Combined or coordinated topical and systemic administration of tetracycline derivatives is also contemplated under the invention. For example, a non-absorbable tetracycline compound can be administered topically, while a tetracycline compound capable of substantial absorption and effective systemic distribution in a subject can be administered systemically.

Photoxicity

In one embodiment, the invention relates to a class of compounds that have low phototoxicity. To identify potentially phototoxic tetracycline derivatives, the 3T3 Neutral Red Phototoxicity assay was employed. The assay is described in Toxicology In Vitro 12:305–327, 1998.

Briefly, 3T3 cells are seeded in to 96-well plates and incubated over night. The growth medium is removed and replaced with phenol-red free Hanks' Balanced Salt Solution containing serial dilutions of the tetracycline derivatives (two plates per compound). After an initial one hour incubation at 37° C., one plate is exposed to 5 Joules/cm$^2$ of UVA/white light from a solar simulator while the other is held in the dark. The plates are then rinsed, re-fed and incubated for 24 hours. Cell visibility is measured by neutral red uptake. Phototoxicity is measured by the relative toxicity between the doses with and without light exposure following published guidelines. (Reference compounds include commercially available tetracycline, doxycycline, and minocycline.) The relative phototoxicity is called photoirritancy factor (PIF). The phototoxic response of the compounds in the present assay is consistent with their behavior in vivo.

The class of low phototoxicity tetracyline derivatives has less than 75% of the phototoxicity of minocycline, preferably less than 70%, more preferably less than 60%, and most preferably 50% or less, wherein the phototoxicity of minocycline is about 2.04. Optimally, the class of low phototoxicity tetracycline derivatives have PIF values of 1. At a PIF value of 1, a compound is considered to have no measurable phototoxicity. Members of this class include, but are not limited to, tetracycline compounds having general forumulae:

STRUCTURE K
wherein: R7, R8, and R9 taken together in each case, have the following meanings:

| R7 | R8 | R9 |
|---|---|---|
| hydrogen | hydrogen | amino |
| hydrogen | hydrogen | palmitamide |
| hydrogen | hydrogen | dimethylamino | and
STRUCTURE L STRUCTURE M
STRUCTURE N STRUCTURE O
wherein: R7, R8, and R9 taken together in each case, have the following meanings:

| R7 | R8 | R9 |
|---|---|---|
| hydrogen | hydrogen | acetamido |
| hydrogen | hydrogen | dimethylaminoacetamido |
| hydrogen | hydrogen | nitro |
| hydrogen | hydrogen | amino | and
wherein R8 and R9 are, respectively, hydrogen and nitro.

The class of low phototoxicity tetracycline compound derivatives includes those derivatives having PIF values greater than 1, i.e. 1 to about 2, preferably 1 to about 1.5. One example is a tetracycline derivative having the general formula:
STRUCTURE K:
wherein: R7, R8, and R9 taken together are, respectively, hydrogen, hydrogen and dimethylamino.

EXAMPLES

The following examples serve to provide further appreciation of the invention but are not meant in any way to restrict the effective scope of the invention.

Example 1

4-Dedimethylamino-7-dimethylamino-6-demethyl-6-deoxy-9-nitrotetracycline Sulfate To a solution of one millimole of 4-dedimethylamino-7-dimethylamino-6-demethyl-6-deoxytetracycline in 25 ml of concentrated sulfuric acid at 0° C. was added 1.05 mmole of potassium nitrate. The resulting solution was stirred at ice bath temperature for 15 minutes and poured in one liter of cold ether with stirring. The precipitated solid was allowed to settle and the majority of solvent decanted. The remaining material was filtered through a sintered glass funnel and the collected solid was washed well with cold ether. The product was dried in a vacuum desiccator overnight.

Example 2

9-amino-4-dedimethylamino-7-dimethylamino-6-demethyl-6-deoxytetracycline Sulfate To a solution of 300 mg of the 9-nitro compound from example 1, in 30 ml of ethanol was added 50 mg of $PtO_2$. The mixture was hydrogenated at atmospheric pressure until the theoretical amount of hydrogen was absorbed. The system is flushed with nitrogen, the catalyst $PtO_2$ is filtered and the filtrate added dropwise to 300 ml of ether. The product that separates is filtered and dried in a vacuum desiccator.

Example 3

9-Acetamido-4-dedimethylamino-7-dimethylamino-6-demethyl-6-deoxytetracycline Sulfate To a well stirred cold solution of 500 mg of 9-amino-4-dedimethylamino-7-dimethylamino-6-demethyl-6-deoxytetracycline sulfate from example 2, in 2.0 ml of 1.3-dimethyl-2-imidazolidinone, 500 mg of sodium bicarbonate was added followed by 0.21 ml of acetyl chloride. The mixture is stirred at room temperature for 30 minutes, filtered and the filtrate was added dropwise to 500 ml of ether. The product that separated was filtered and dried in a vacuum desiccator.

Example 4

4-Dedimethylamino-7-dimethylamino-6-demethyl-6-deoxy-9-diazoniumtetracycline Sulfate To a solution of 0.5 g of 9-amino-4-dedimethylamino-7-dimethylamino-6-demethyl-6-deoxytetracycline sulfate, from example 2, in 10 ml of 0.1N hydrochloric acid in methanol cooled in an ice bath, 0.5 ml of n-butyl nitrite was added. The solution was stirred at ice bath temperature for 30 minutes and then poured into 250 ml of ether. The product that separated was filtered, washed with ether and dried in a vacuum desiccator.

Example 5

9-Azido-4-dedimethylamino-7-dimethylamino-6-demethyl-6-deoxytetracycline Sulfate To a solution of 0.3 mmole of 4-dedimethylamino-7-dimethylamino-6-demethyl-6-deoxy-9-diazoniumtetracycline sulfate, from example 4, 10 ml of 0.1 N methanolic hydrogen chloride was added 0.33 mmole of sodium azide. The mixture was stirred at room temperature for 1.5 hours. The reaction mixture was then poured into 200 ml of ether. The product that separated was filtered and dried in a vacuum desiccator.

Example 6

9-Amino-8-chloro-4-dedimethylamino-7-dimethylamino-6-demethyl-6-deoxy-tetracycline Sulfate One gram of 9-azido-4-dedimethylamino-7-dimethylamino-6-demethyl-6-deoxytetracycline hydrochloride, from example 4, was dissolved in 10 ml of concentrated sulfuric acid saturated with HCL at 0° C. The mixture was stirred at ice bath temperature for 1.5 hours and then slowly added dropwise to 500 ml of cold ether. The product that separated was filtered, washed with ether and dried in a vacuum desiccator.

Example 7

4-Dedimethylamino-7-dimethylamino-6-demethyl-6-deoxy-9-ethoxythiocarbonylthio-tetracycline Sulfate A solution of 1.0 mmole of 4-dedimethylamino-7-dimethylamino-6-demethyl-6-deoxy-9-diazoniumtetracycline sulfate, from example 4, in 15 ml of water was added to a solution of 1.15 mmole of potassium ethyl xanthate in 15 ml of water. The mixture was stirred at room temperature for one hour. The product separated and was filtered and dried in a vacuum desiccator.

Example 8A

General Procedure for Nitration

To 1 mmole of a 4-dedimethylamino-6-deoxytetracycline in 25 ml of concentrated sulfuric acid at 0° C. was added 1 mmole of potassium nitrate with stirring. The reaction solution was stirred for 15 minutes and then poured into 100 g of chopped ice. The aqueous solution was extracted 5 times with 20 ml of butanol each time. The butanol extracts were washed three times with 10 ml of water each time, and concentrated in vacuo to a volume of 25 ml. The light yellow crystalline solid which precipitated was filtered, washed with 2 ml of butanol and dried in vacuo at 60° C. for 2 hours. This solid was a mixture of the two mononitro isomers.

Example 8B

4-Dedimethylamino-6-deoxy-9-nitrotetracycline

To 980 mg of the nitration product from 4-dedimethylamino-6-deoxytetracycline (a mixture of the 2 isomers) in 25 ml of methanol was added enough triethylamine to dissolve the solid. The filtered solution (pH 9.0) was adjusted to pH 5.2 with concentrated sulfuric acid. A crystalline yellow solid (236 mg.) was obtained (29% yield). The material at this point was quite pure and contained only small amounts of the 7-isomer. Final purification was accomplished by liquid partition chromatography using a diatomaceous earth packed column and the solvent system: chloroform: butanol: 0.5 M phosphate buffer (pH 2) (16:1:10).

Example 9

4-Dedimethylamino-6-deoxy-7-nitrotetracycline

The methanol filtrate from example 8 was immediately adjusted to pH 1.0 with concentrated sulfuric acid. The light yellow crystalline solid, which was obtained as the sulfate salt. A purified free base was obtained by adjusting an aqueous solution of the sulfate salt (25 mg/ml) to pH 5.2 with 2 N sodium carbonate.

Example 10

9-Amino-4-dedimethylamino-6-deoxytetracycline

To a solution of 300 mg of the 9-nitro compound, prepared in example 8, in 30 ml of ethanol was added 50 mg of $PtO_2$. The mixture was hydrogenated at atmospheric pressure until the theoretical amount of hydrogen was absorbed. The system is flushed with nitrogen, the $PtO_2$ catalyst is filtered and the filtrate added dropwise to 300 ml of ether. The solid that separates is filtered and dried in a vacuum desiccator.

Example 11

9-Acetamido-4-dedimethylamino-6-deoxytetracycline Sulfate

To well stirred cold solution of 500 mg of 9-amino-4-dedimethylamino-6-deoxytetracycline sulfate, from example 10, in 2.0 ml of 1,3-dimethyl-2-imidazolidinone was added 500 mg of sodium bicarbonate followed by 0.21 ml of acetyl chloride. The mixture was stirred at room temperature for 30 minutes, filtered and the filtrate was added dropwise to 500 ml of ether. The solid that separated was filtered and dried in a vacuum desiccator.

Example 12

4-Dedimethylamino-6-deoxy-9-diazoniumtetracycline Sulfate

To a solution of 0.5 g of 9-amino-4-dedimethylamino-6-deoxytetracycline sulfate, from example 10, in 10 ml of 0.1N hydrochloric acid in methanol cooled in an ice bath was added 0.5 ml of n-butyl nitrite. The solution was stirred at ice bath temperature for 30 minutes and the poured into 250 ml of ether. The solid that separated was filtered, washed with ether and dried in a vacuum desiccator.

Example 13

9-Azido-4-dedimethylamino-6-deoxytetracycline Sulfate

To a solution of 0.3 mmole of 4-dedimethylamino-6-deoxy-9-diazoniumtetracycline sulfate, of example 12, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 14

9-Amino-8-chloro-4-dedimethylamino-6-deoxytetracycline Sulfate

One gram of 9-azido-4-dedimethylamino-7-dimethylamino-6-deoxytetracycline hydrochloride, from example 13, was dissolved in 10 ml of concentrated sulfuric acid saturated with HCL at 0° C. The mixture was stirred at ice bath temperature for 1.5 hours and then slowly added dropwise to 500 ml of cold ether. The solid that separated was filtered, washed and ether and dried in a vacuum desiccator.

Example 15

4-Dedimethylamino-6-deoxy-9-ethoxythiocarbonylthiotetracycline Sulfate

A solution of 1.0 mmole of 4-dedimethylamino-6-deoxy-9-diazoniumtetracycline sulfate, from example 12, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 16

9-Dimethylamino-4-dedimethylamino-6-deoxytetracycline Sulfate

To a solution of 100 mg. of the 9-amino compound from example 10, in 10 ml of ethylene glycol monomethyl ether is added 0.05 ml of concentrated sulfuric acid, 0.4 ml. of a 40% aqueous formaldehyde solution and 100 mg of a 10% palladium on carbon catalyst. The mixture is hydrogenated under atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried, yield, 98 mg.

Example 17

7-Amino-4-dedimethylamino-6-deoxytetracycline

This compound can be made using Procedure A or B.
Procedure A. To a solution of 300 mg of the 7-nitro compound, from example 1, in 30 ml of ethanol was added 50 mg of $PtO_2$. The mixture was hydrogenated at atmospheric pressure until the theoretical amount of hydrogen was absorbed. The system is flushed with nitrogen, the catalyst $PtO_2$ is filtered and the filtrate added dropwise to 300 ml of ether. The solid that separates is filtered and dried in a vacuum desiccator.

Procedure B. 1 g of 6-deoxy-4-dedimethylamino-tetracycline was dissolved in 7.6 ml THF and 10.4 ml methanesulfonic acid at −10° C. After warming the mixture to 0° C. a solution of 0.86 g of dibenzyl azodicarboxylate was added and the mixture stirred for 2 hours at 0° C. to yield 7-[1,2-bis(carbobenzyloxy)hydrazino]-4-dedimethylamino-6-deoxytetracycline. A solution of 1 millimole of this material in 70 ml 2-methoxyethanol, and 300 mg 10% Pd—C was hydrogenated at room temperature to give 7-amino-6-deoxy-4-dedimethylaminotetracycline.

Example 18

7-Amino-6-deoxy-5-hydroxy-4-dedimethylaminotetracycline 1 g of 6-deoxy-5-hydroxy-4-dedimethylaminotetracycline 3 was dissolved in 7.6 ml THF and 10.4 ml methanesulfonic acid at −10° C. After warming the mixture to 0° C. a solution of 0.86 g dibenzyl azodicarboxylate in 0.5 ml THF was added and the mixture stirred for 2 hours at 0° C. to yield 7-[1,2-bis(carbobenzyloxy)hydrazino]-4-dedimethylamino-6-deoxy-5-hydroxytetracycline. A solution of 1 millimole of this material in 70 ml 2-methoxyethanol, and 300 mg 10% Pd—C was hydrogenated at room temperature to give 7-amino-6-deoxy-5-hydroxytetracycline.

Example 19

7-Acetamido-4-dedimethylamino-6-deoxy-5-hydroxytetracycline Sulfate

To well stirred cold solution of 500 mg of 7-amino-4-dedimethylamino-6-deoxy-5-hydroxytetracycline sulfate, from example 18, in 2.0 ml of 1,3-dimethyl-2-imidazolidinone was added 500 mg of sodium bicarbonate followed by 0.21 ml of acetyl chloride. The mixture was stirred at room temperature for 30 minutes, filtered and the filtrate was added dropwise to 500 ml of ether. The solid that separated was filtered and dried in a vacuum desiccator.

Example 20

4-Dedimethylamino-6-deoxy-5-hydroxy-7-diazoniumtetracycline Hydrochloride

To a solution of 0.5 g of 7-amino-4-dedimethylamino-6-deoxy-5-hydroxytetracycline sulfate, from example 20, in 10 ml of 0.1N hydrochloric acid in methanol cooled in an ice bath was added 0.5 ml of n-butyl nitrite. The solution was stirred at ice bath temperature for 30 minutes and then poured into 250 ml of ether. The solid that separated was filtered, washed with ether and dried in a vacuum desiccator.

Example 21

7-Azido-4-dedimethylamino-6-deoxy-5-hydroxytetracycline

To a solution of 0.3 mmole of 4-dedimethylamino-6-deoxy-5-hydroxy-7-diazoniumtetracycline hydrochloride, from example 20, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 22

7-Amino-8-chloro-4-dedimethylamino-6-deoxy-5-hydroxytetracycline Sulfate

One gram of 7-azido-4-dedimethylamino-7-dimethylamino-6-deoxy-5-hydroxytetracycline sulfate, from example 21, was dissolved in 10 ml of concentrated sulfuric acid (previously saturated with hydrogen chloride) at 0° C. The mixture was stirred at ice bath temperature for 1.5 hours and then slowly added dropwise to 500 ml of cold ether. The solid that separated was filtered, washed with ether and dried in a vacuum desiccator.

Example 23

4-Dedimethylamino-6-deoxy-5-hydroxy-7-ethoxythiocarbonylthiotetracycline

A solution of 1.0 mmole of 4-dedimethylamino-6-deoxy-5-hydroxy-7-diazoniumtetracycline hydrochloride, from example 20, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 24

7-Dimethylamino-4-dedimethylamino-6-deoxy-5-hydroxytetracycline Sulfate

To a solution of 100 mg of the 7-amino compound in 10 ml of ethylene glycol monomethyl ether is added 0.05 ml of concentrated sulfuric acid, 0.4 ml of a 40% aqueous formaldehyde solution and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried, yield, 78 mg.

Example 25

7-Diethylamino-4-dedimethylamino-5-hydroxytetracycline Sulfate

To a solution of 100 mg of the 7-amino compound in 10 ml of ethylene glycol monomethyl ether is added 0.05 ml of concentrated sulfuric acid, 0.4 ml of acetaldehyde and 100 mg of a 10% palladium on carbon catalyst. The mixture is reduced with hydrogen at atmospheric pressure at room temperature for 20 minutes. The catalyst was filtered and filtrate was evaporated to dryness under reduced pressure. The residue is dissolved in 5 ml of methanol and this solution was added to 100 ml of ether. The product that separated was filtered and dried.

Example 26

4-Dedimethylamino-6-deoxy-7-diazoniumtetracycline Hydrochloride

To a solution of 0.5 g. of 7-amino-4-dedimethylamino-6-deoxytetracycline sulfate, from example 17, in 10 ml of 0.1N hydrochloric acid in methanol cooled in an ice bath was added 0.5 ml of n-butyl nitrite. The solution was stirred at ice bath temperature for 30 minutes and then poured into 250 ml of ether. The solid that separated was filtered, washed with ether and dried in a vacuum desiccator.

Example 27

7-Azido-4-dedimethylamino-6-deoxytetracycline

To a solution of 0.3 mmole of 4-dedimethylamino-6-deoxy-7-diazoniumtetracycline hydrochloride, from example 26, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 28

7-Amino-8-chloro-4-dedimethylamino-6-deoxytetracycline Sulfate

One gram of 7-azido-4-dedimethylamino-7-dimethylamino-6-deoxytetracycline sulfate was dissolved in 10 ml of concentrated sulfuric acid (previously saturated with hydrogen chloride) at 0° C. The mixture was stirred at ice bath temperature for 1.5 hours and then slowly added dropwise to 500 ml of cold ether. The solid that separated was filtered, washed with ether and dried in a vacuum desiccator.

Example 29

4-Dedimethylamino-6-deoxy-7-ethoxythiocarbonylthiotetracycline

A solution of 1.0 mmole of 4-dedimethylamino-6-deoxy-7-diazoniumtetracycline hydrochloride, from example 26, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 30

7-Dimethylamino-4-dedimethylamino-6-deoxytetracycline Sulfate

To a solution of 100 mg of the 7-amino compound, from example 26, in 10 ml of ethylene glycol monomethyl ether is added 0.05 ml of concentrated sulfuric acid, 0.4 ml of a 40% aqueous formaldehyde solution and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried.

Example 31

9-Acetamido-8-chloro-4-dedimethylamino-7-dimethylamino-6-deoxy-6-demethyltetracycline To well stirred cold solution of 500 mg of 9-amino-8-chloro-4-dedimethylamino-6-deoxy-6-demethyl-7-dimethyl amino tetracycline sulfate, from example 6, in 2.0 ml of 1,3-dimethyl-2-imidazolidinone was added 500 mg of sodium bicarbonate followed by 0.21 ml. of acetyl chloride. The mixture was stirred at room temperature for 30 minutes, filtered and the filtrate was added dropwise to 500 ml of ether. The solid that separated was filtered and dried in a vacuum desiccator.

Example 32

8-Chloro-4-dedimethylamino-7-dimethylamino-6-deoxy-6-demethyl-9-ethoxythiocarbonylthiotetracycline A solution of 1.0 mmole of -8-chloro-4-dedimethylamino-6-deoxy-6-demethyl-7-dimethyl amino-9-diazoniumtetracycline hydrochloride in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 33

8-Chloro-9-dimethylamino-4-dedimethylamino-7-dimethylamino-6-deoxy-6-demethytetracycline Sulfate To a solution of 100 mg. of the 9-amino compound, from example 6, in 10 ml of ethylene glycol monomethyl ether is added 0.05 ml of concentrated sulfuric acid, 0.4 ml of acetaldehyde and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried.

Example 34

N-(4-methylpiperazin-1-yl) methyl-4-dedimethylamino-6-demethyl-6-deoxytetracycline An aqueous solution of 58 mg (37%) formaldehyde (0.72 mmol) was added to a solution of 203 mg (0.49 mmol) of 4-dedimethylamino-6-demethyl-6-deoxytetracycline in 5.0 ml ethylene glycol dimethyl ether. The mixture was stirred at room temperature for 0.5 hours. 56 mg (0.56 mmol) of 1-methylpiperazine was then added and the resulting mixture was stirred overnight and refluxed for 20 minutes. The mixture was then cooled and a solid product was collected by filtration. The solid product was then washed with the solvent and dried by vacuum filtration.

Example 35

N-(4-methylpiperazin-1-yl)methyl-4-dedimethylamino-6-demethyl-6-deoxy-9-hexanoylaminotetracycline An aqueous solution of 49 mg 37% formaldehyde (0.60 mmol) was added to a solution of 146 mg (0.30 mmol) of 4-dedimethylamino-6-demethyl-6-deoxy-9-hexanoylaminotetracycline in 5.0 ml ethylene glycol dimethyl ether. The mixture was stirred at room temperature for 0.5 hours. 60 mg (0.60 mmol) of 1-methylpiperazine was then added and the resulting mixture was stirred overnight and refluxed for 20 minutes. The mixture was then cooled and a solid product was collected by filtration. The solid product was then washed with the solvent and dried by vacuum filtration.

Example 36

4-Dedimethylamino-6-demethyl-6-deoxy-9-hexanoylaminotetracycline 1.54 g (7.2 mmol) of hexanoic anhydride and 150 mg of 10% Pd/C catalyst were added to 300 mg (0.72 mmol) of 4-dedimethylamino-6-demethyl-6-deoxytetracycline in 6.0 ml of 1,4-dioxane and 6.0 ml of methanol. The mixture was hydrogenated overnight at room temperature. The catalyst was removed by filtration and the filtrate was concentrated under reduced pressure. The residue was dissolved in 7 ml of ethyl acetate and triturated with 50 ml of hexane to produce a solid product. The solid product was filtered and dried by vacuum filtration.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

Example 37

Phototoxicity Determination

BALB/c 3T3 (CCL-163) cells were obtained from ATCC and cultured in antibiotic-free Dulbecco's Minimum Essential Medium (4.5 g/l glucose)(DMEM) supplemented with L-glutamine (4 mM) and 10% newborn calf serum. The working cell bank was prepared and found to be free of mycoplasma. Streptomycin sulfate (100 µg/ml) and penicillin (100 IU/ml) were added to the medium after the cells were treated with test article in 96-well plates.

Serial dilutions of the tetracycline derivatives were prepared in DMSO at concentrations 100× to final testing concentration. The CMT dilutions in DMSO were then diluted in Hanks' Balanced Salt Solution (HBSS) for application to the cells. The final DMSO concentration was 1% in treated and control cultures. For the dose range finding assay, 8 serial dilutions covered a range of 100 to 0.03 mg/ml in half log steps while the definitive assays used 6 to 8 doses prepared in quarter log steps, centered on the expected 50% toxicity point. In many cases, the dose range for treatment without UV light was different from the dose range selected with UV light. One hundred µg/ml is the highest dose recommended to prevent false negative results from UV absorption by the dosing solutions.

Controls: Each assay included both negative (solvent) and positive controls. Twelve wells of negative control cultures were used on each 96-well plate. Chlorpromazine (Sigma) was used as the positive control and was prepared and dosed like the test tetracycline derivatives.

Solar Simulator: A Dermalight SOL 3 solar simulator, equipped with a UVA H1 filter (320–400 nm), was adjusted to the appropriate height. Measurement of energy through the lid of a 96-well microtiter plate was carried out using a calibrated UV radiometer UVA sensor. Simulator height was adjusted to deliver 1.7±0.1 m/Wcm$^2$ of UVA energy (resulting dose was 1J/cm$^2$ per 10 min.)

Phototoxicity Assay: Duplicate plates were prepared for each test material by seeding 10$^4$ 3T3 cells per well in µl of complete medium 24 hours before treatment. Prior to treatment, the medium was removed, and the cells washed once with 125 µl prewarmed HBSS. Fifty µl of prewarmed HBSS were added to each well. Fifty µl of test article dilutions were added to the appropriate wells and the plates returned to the incubator for approximately one hour. Following the 1 hr incubation, the plates designated for the photoirritation assay were exposed (with the lid on) to 1.7±0.1 mW/cm$^2$ UVA light for 50±2 minutes at room temperature resulting in an irradiation dose of 5J/cm2. Duplicate plates designated for the cytotoxicity assay were kept in the dark room temperature for 50±2 minutes. After the 50 minute exposure period the test article dilutions were decanted from the plates and the cells washed once with 125 µl HBSS. One hundred µl of medium were added to all wells and the cells incubated as above for 24±1 hours.

After 24 hours of incubation, the medium was decanted and 100 µl of the Neutral Red containing media added to each well. The plates were returned to the incubator and incubated for approximately 3 hours. After 3 hours, the medium was decanted and each well rinsed once with 250 µl of HBSS. The plates were blotted to remove the HBSS and 100 µl of Neutral Red Solvent were added to each well. After a minimum of 20 minutes of incubation at room temperature (with shaking), the absorbance at 550 nm was measured with a plate reader, using the mean of the blank outer wells as the reference. Relative survival was obtained by comparing the amount of neutral red taken by test article and positive control treated groups to the neutral red taken up by the negative group on the same plate. IC$_{50}$ values for both the UVA exposed and non-exposed groups were determined whenever possible. One dose range finding and at least two definitive trails were performed on each tetracycline derivative and control compound.

Determination of Phototoxicity: Phototoxicity of the tetracycline derivatives can be measured by its photoirritancy factor (PIF). The PIF was determined by comparing the IC$_{50}$ without UVA [IC$_{50}$(−UVA)] with the IC$_{50}$ with UVA [IC$_{50}$(+UVA)]:

$$PIF = \frac{IC_{50}(-UVA)}{IC_{50}(+UVA)}$$

If both IC$_{50}$ values can be determined, the cut off value of the factor to discriminate between phototoxicants and non-phototoxicants is a factor of 5. A factor greater than 5 is indicative of phototoxic potential of the test material.

If IC$_{50}$ (+UVA) can be determined but IC$_{50}$(−UVA) cannot, the PIF cannot be calculated, although the compound tested may have some level of phototoxic potential. In this case, a ">PIF" can be calculated and the highest testable dose (−UVA) will be used for calculation of the ">PIF."

$$>PIF = \frac{\text{maximum dose}(-UVA)}{IC_{50}(+UVA)}$$

If both, IC$_{50}$(+UVA) and IC$_{50}$(+UVA) cannot be calculated because the chemical does not show cytotoxicty (50% reduction in viability) up to the highest dose tested, this would indicate a lack of phototoxic potential.

INDEX OF STRUCTURES

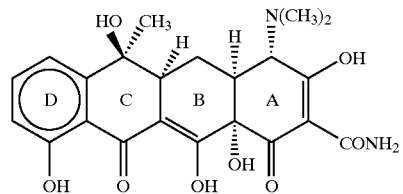

Structure A

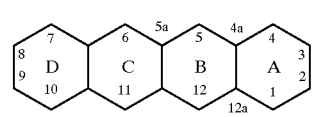

Structure B

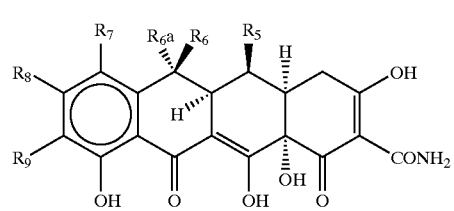

Structure C

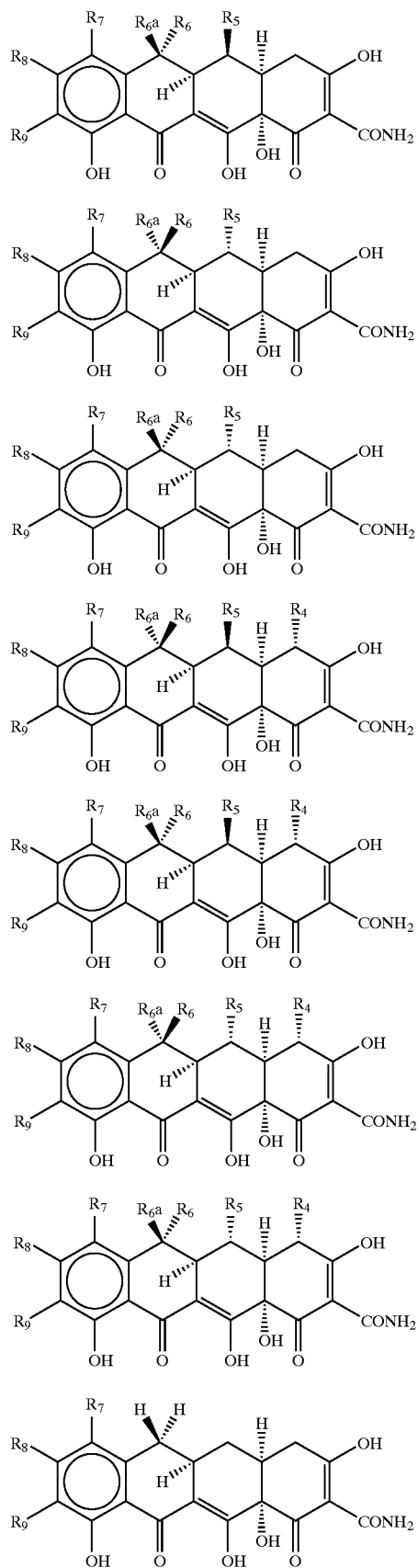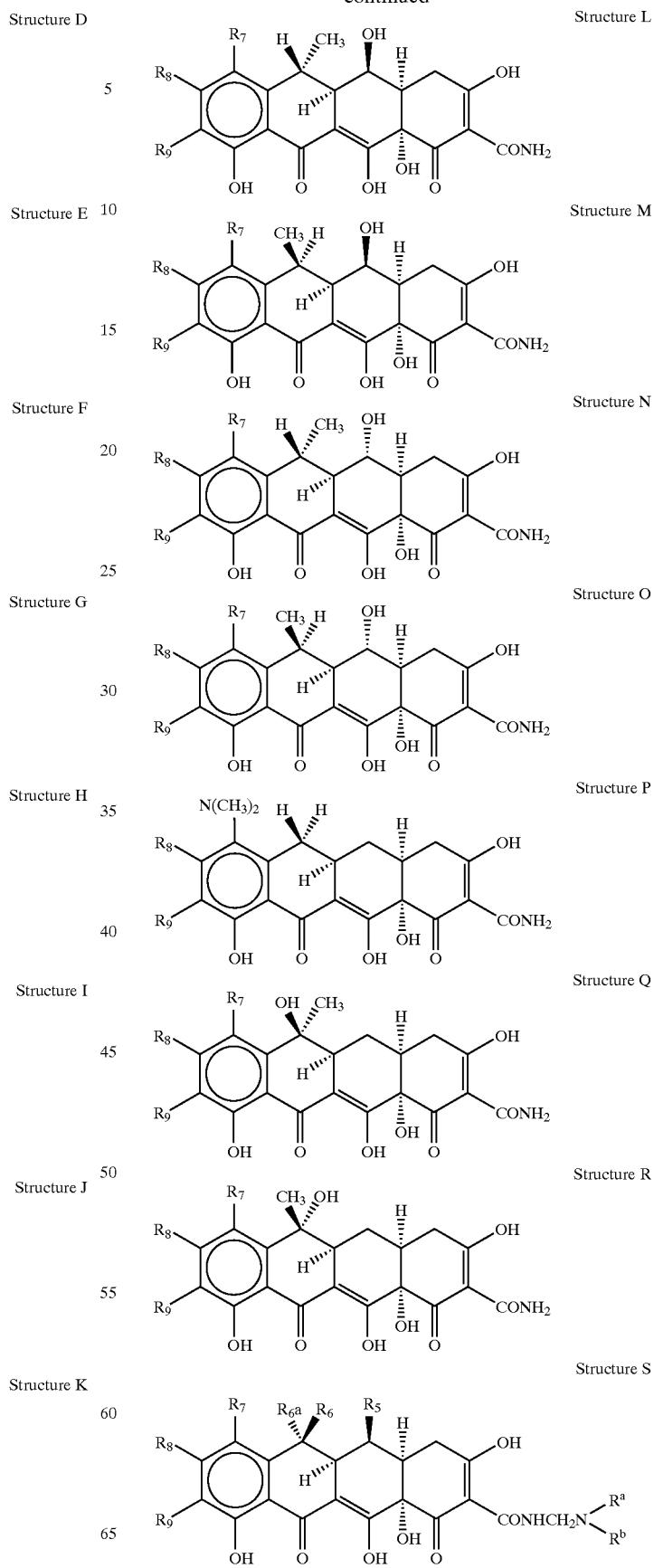

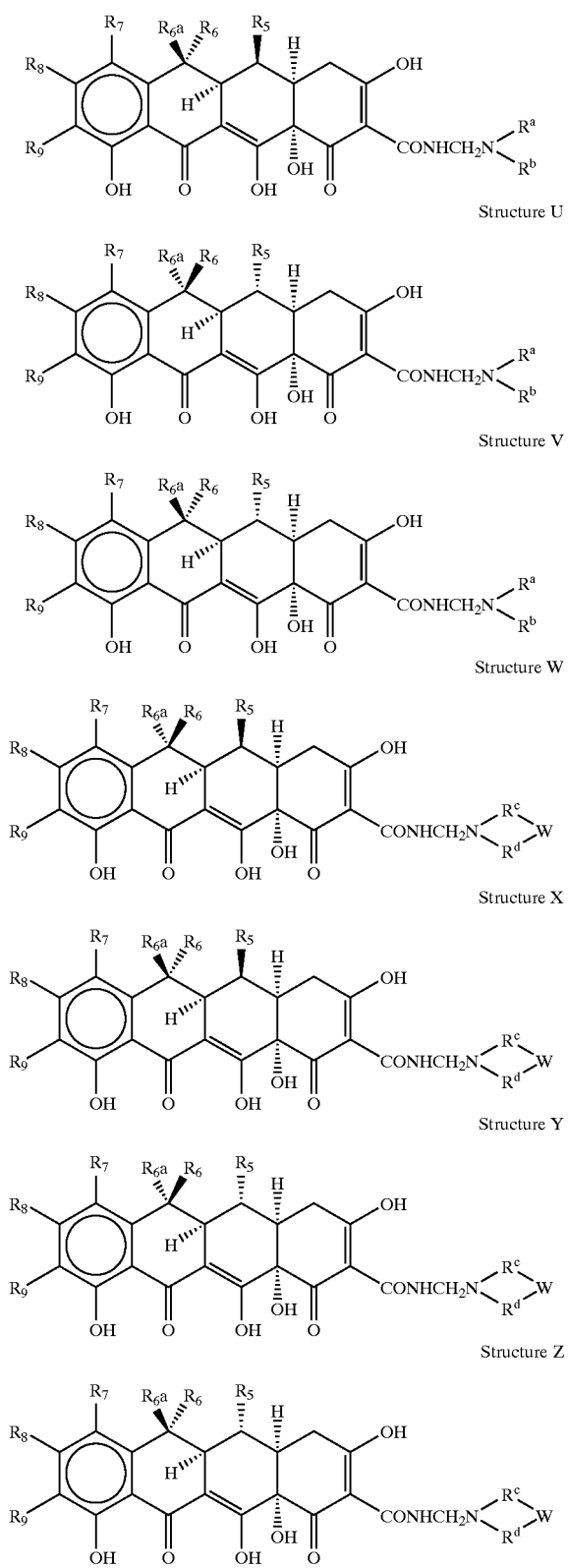

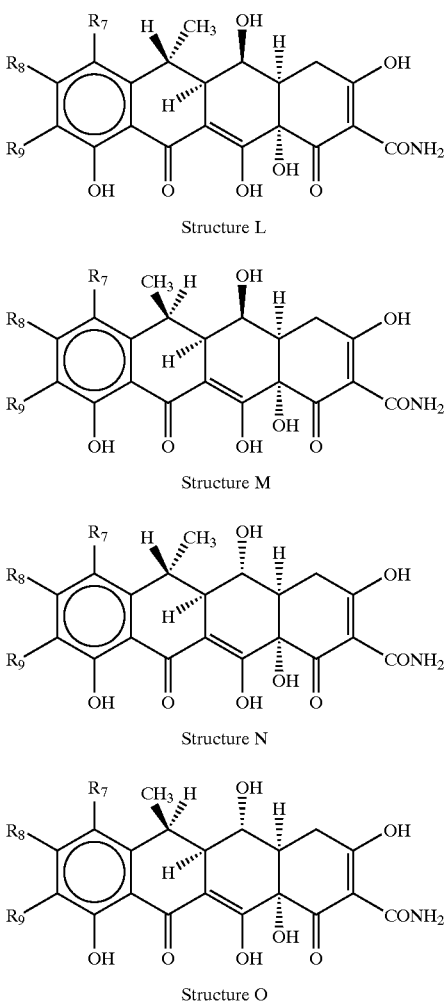

What is claimed is:

1. A 4-de(dimethylamino)doxycycline compound having structure L, M, N, or O wherein: R7, R8, and R9 taken together in each case, have the following meanings:

| R7 | R8 | R9 | |
|---|---|---|---|
| hydrogen | hydrogen | palmitamide | (COL-803) |
| hydrogen | hydrogen | nitro | (COL-804) |
| hydrogen | hydrogen | amino | (COL-805). |

2. A 4-de(dimethylamino)doxycycline compound according to claim 1, wherein R7 is hydrogen, R8 is hydrogen and R9 is palmitamide (COL-803).

3. A 4-de(dimethylamino)doxycycline compound according to claim 1, wherein R7 is hydrogen, R8 is hydrogen and R9 is nitro (COL-804).

4. A 4-de(dimethylamino)doxycycline compound according to claim 1, wherein R7 is hydrogen, R8 is hydrogen and R9 is amino (COL-805).

* * * * *